United States Patent [19]

Cramp et al.

[11] Patent Number: 5,374,606
[45] Date of Patent: Dec. 20, 1994

[54] 4-BENZOYLISOXAZOLE HERBICIDES

[75] Inventors: Susan M. Cramp, Ongar, England; Claude Lambert, Lyons, France; Gillian M. Little, Essex; John Morris, Ongar, both of England

[73] Assignee: Rhone-Poulenc Agriculture Limited, Essex, England

[21] Appl. No.: 191,550

[22] Filed: Feb. 3, 1994

[30] Foreign Application Priority Data

Feb. 3, 1993 [GB] United Kingdom ............... 9302049

[51] Int. Cl.$^5$ .................... A01N 43/80; C07D 261/08
[52] U.S. Cl. .................................... 504/270; 548/248
[58] Field of Search .................. 548/248; 504/270

[56] References Cited
FOREIGN PATENT DOCUMENTS

| 0418175 | 3/1991 | European Pat. Off. | ............ 548/248 |
| 0487357 | 5/1992 | European Pat. Off. | ............ 548/248 |
| 0527036 | 2/1993 | European Pat. Off. | ............ 548/248 |
| 0527037 | 2/1993 | European Pat. Off. | ............ 548/248 |

Primary Examiner—Patricia L. Morris
Assistant Examiner—Joseph K. McKane
Attorney, Agent, or Firm—Burns, Doane, Swecker & Mathis

[57] ABSTRACT

The invention relates to 4-benzoylisoxazole derivatives of formula (I):

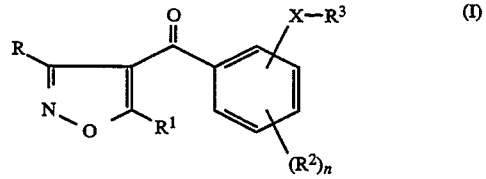

wherein:
R represents the hydrogen atom or a group $-CO_2R^4$;
$R^1$ represents alkyl, haloalkyl or optionally substituted cycloalkyl;
$R^2$ represents halogen, optionally halogenated alkyl, alkenyl or alkynyl, alkyl substituted by one or more groups $-OR^5$; or a group selected from nitro, cyano, $-CO_2R^5$, $-S(O)_pR^6$, $-O(CH_2)_mOR^5$, $-COR^5$, $-NR^{61}R^{62}$, $-N(R^8)SO_2R^7$, $-OR^5$, $-OSO_2R^7$ and $-(CR^9R^{10})_r-S(O)_qR^7$;
$R^3$ represents $-S(O)_qR^7$;
X represents $-(CR^9R^{10})_r-$;
n represents zero or an integer from one to four;
$R^4$ represents alkyl or haloalkyl;
$R^5$ represents optionally halogenated alkyl, alkenyl or alkynyl;
$R^6$, $R^{61}$ and $R^{62}$, which may be the same or different, each represents alkyl, haloalkyl or optionally substituted phenyl;
$R^7$ represents optionally halogenated alkyl, alkenyl or alkynyl, or optionally substituted phenyl or benzyl;
$R^8$ represents hydrogen or optionally halogenated alkyl, alkenyl or alkynyl;
$R^9$ and $R^{10}$, which may be the same or different, each represents hydrogen, alkyl, haloalkyl or optionally substituted phenyl;
p represents zero, one or two;
q represents zero, one or two;
m represents 1, 2 or 3;
t represents an integer from one to four;
or an agriculturally acceptable salt thereof; and to their use as herbicides.

33 Claims, No Drawings

4-BENZOYLISOXAZOLE HERBICIDES

This invention relates to novel 4-benzoylisoxazole derivatives, compositions containing them, processes for their preparation, intermediates in their preparation and their use as herbicides.

Herbicidal 4-benzoylisoxazoles are described in European Patent Publication Number 0418175.

The present invention provides 4-benzoylisoxazole derivatives of formula (I):

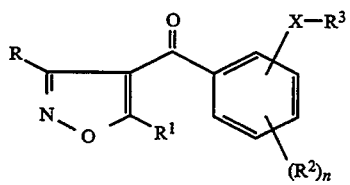

wherein:

R represents the hydrogen atom or a group $-CO_2R^4$;

$R^1$ represents:
- a straight- or branched-chain alkyl group containing up to six carbon atoms which is optionally substituted by one or more halogen atoms; or
- a cycloalkyl group containing from three to six carbon atoms optionally substituted by one or more groups $R^5$ or one or more halogen atoms;

$R^2$ represents:
- a halogen atom; or
- a straight- or branched-chain alkyl group containing up to six carbon atoms which is optionally substituted by one or more halogen atoms;
- a straight- or branched-chain alkenyl or alkynyl group containing up to six carbon atoms which is optionally substituted by one or more halogen atoms;
- a straight- or branched-chain alkyl group containing up to six carbon atoms which is substituted by one or more groups $-OR^5$; or
- a group selected from nitro, cyano, $-CO_2R^5$, $-S(O)_pR^6$, $-O(CH_2)_mOR^5$, $-COR^5$, $-NR^{61}R^{62}$, $-N(R^8)SO_2R^7$, $-OR^5$, $-OSO_2R^7$ and $-(CR^9R^{10})_r-S(O)_qR^7$;

$R^3$ represents $-S(O)_qR^7$;

X represents $-(CR^9R^{10})_r-$;

n represents zero or an integer from one to four; when n is greater than one the groups $R^2$ may be the same or different;

$R^4$ represents a straight- or branched-chain alkyl group containing up to 6 carbon atoms which is optionally substituted by one or more halogen atoms;

$R^5$ represents:
- a straight- or branched-chain alkyl group containing up to 6 carbon atoms which is optionally substituted by one or more halogen atoms; or
- a straight- or branched-chain alkenyl or alkynyl group containing from three to six carbon atoms which is optionally substituted by one or more halogen atoms;

$R^6$, $R^{61}$ and $R^{62}$, which may be the same or different, each represents:
a straight- or branched-chain alkyl group containing up to 6 carbon atoms which is optionally substituted by one or more halogen atoms;
phenyl optionally substituted by from one to five groups $R^2$ which may be the same or different;

$R^7$ represents:
- a straight- or branched-chain alkyl group containing up to 6 carbon atoms which is optionally substituted by one or more halogen atoms;
- a straight- or branched-chain alkenyl or alkynyl group containing from three to six carbon atoms which is optionally substituted by one or more halogen atoms;
- or $-(CR^{51}R^{52})_u-$[phenyl optionally substituted by from one to five groups which may be the same or different selected from halogen; nitro; cyano; a straight- or branched-chain alkyl or alkoxy group containing up to 6 carbon atoms which is optionally substituted by one or more halogen atoms; and $-S(O)_pR^4$];

$R^8$ represents:
- the hydrogen atom;
- a straight- or branched-chain alkyl, alkenyl or alkynyl group containing up to ten carbon atoms which is optionally substituted by one or more halogen atoms;

$R^9$ and $R^{10}$, which may be the same or different, each represents:
- the hydrogen atom;
- a straight- or branched-chain alkyl group containing up to 6 carbon atoms which is optionally substituted by one or more halogen atoms; or
- phenyl optionally substituted by from one to five groups $R^2$ which may be the same or different;

$R^{51}$ and $R^{52}$, which may be the same or different, each represents:
- the hydrogen atom;
- a straight- or branched-chain alkyl group containing up to 6 carbon atoms which is optionally substituted by one or more halogen atoms;

p represents zero, one or two;
q represents zero, one or two;
m represents 1, 2 or 3;
t represents an integer from one to four; when t is greater than one the groups $-CR^9R^{10}-$ may be the same or different;
u represents zero or one;

and agriculturally acceptable salts thereof, which possess valuable herbicidal properties.

In certain cases the groups R to $R^{10}$, $R^{51}$, $R^{52}$, $R^{61}$ and $R^{62}$ may give rise to optical and/or stereoisomerism. All such forms are embraced by the present invention.

By the term "agriculturally acceptable salts" is meant salts the cations or anions of which are known and accepted in the art for the formation of salts for agricultural or horticultural use. Preferably the salts are water-soluble. Suitable acid addition salts, formed by compounds of formula I containing an amino group, include salts with inorganic acids, for example hydrochlorides, sulphates, phosphates and nitrates and salts with organic acids, for example acetic acid.

It will be understood that in the above definition $R^2$ does not include substituents containing two or more phenyl rings linked through a bridging group.

The compounds of the invention, in some aspects of their activity, for example in their control of important weeds, for example *Amaranthus retroflexus, Echinochloa crus-galli, Setaria viridis, Setaria faberii*, and *Avena fatua*, show advantages over known compounds.

A preferred class of compounds of formula (I) are those wherein:

$R^2$ represents:
  a halogen atom;
  a straight- or branched-chain alkyl group containing up to six carbon atoms which is optionally substituted by one or more halogen atoms;
  a straight- or branched-chain alkyl group containing up to six carbon atoms which is substituted by one or more groups $-OR^5$; or
  a group selected from nitro, cyano, $-CO_2R^5$, $-S(O)_pR^6$, $-O(CH_2)_mOR^5$, $-COR^5$, $-NR^{61}R^{62}$, $-N(R^8)SO_2R^7$, $-OR^5$ and $-OSO_2R^7$;
$R^5$ represents a straight- or branched-chain alkyl group containing up to 6 carbon atoms which is optionally substituted by one or more halogen atoms; and
$R^7$ represents a straight- or branched-chain alkyl group containing up to 6 carbon atoms which is optionally substituted by one or more halogen atoms.

A further preferred class of compounds of formula (I) are those wherein:
$R^1$ represents:
  a straight- or branched-chain alkyl group containing from one to three carbon atoms; or
  a cyclopropyl or 1-methylcyclopropyl group;
$R^2$ represents:
  a halogen atom;
  a straight- or branched-chain alkyl group containing up to 4 carbon atoms which is optionally substituted by one or more halogen atoms;
  a straight- or branched-chain alkyl group containing up to 4 carbon atoms which is substituted by one or more groups $-OR^5$; or
  a group selected from nitro, cyano, $-CO_2R^5$, $-S(O)_pR^6$, $-O(CH_2)_mOR^5$, $-NR^{61}R^{62}$, $-N(R^8)SO_2R^7$, $-OR^5$ and $-OSO_2R^7$;
$R^4$ represents a straight- or branched-chain alkyl group containing up to 6 carbon atoms which is optionally substituted by one or more halogen atoms;
$R^5$ and $R^6$ which may be the same or different, each represents a straight- or branched-chain alkyl group containing up to 4 carbon atoms which is optionally substituted by one or more halogen atoms;
$R^{61}$ and $R^{62}$ which may be the same or different, each represents a straight- or branched-chain alkyl group containing up to 6 carbon atoms;
$R^7$ represents a straight- or branched-chain alkyl group containing up to 4 carbon atoms which is optionally substituted by one or more halogen atoms;
$R^8$ represents a straight- or branched-chain alkyl, alkenyl or alkynyl group containing up to 4 carbon atoms which is optionally substituted by one or more halogen atoms;
$R^9$ and $R^{10}$, which may be the same or different, each represents:
  the hydrogen atom; or
  a straight- or branched-chain alkyl group containing up to 6 carbon atoms which is optionally substituted by one or more halogen atoms;
n represents zero, one or two; and
t represents one.

A further preferred class of compounds of formula (I) are those wherein:
$R^2$ represents:
  a halogen atom;
  a straight- or branched-chain alkyl group containing up to 4 carbon atoms which is optionally substituted by one or more halogen atoms;
  a straight- or branched-chain alkyl group containing up to 4 carbon atoms which is substituted by one or more groups $-OR^5$; or
  a group selected from nitro, $-CO_2R^5$, $-S(O)_pR^6$, $-O(CH_2)_mOR^5$, $-NR^{61}R^{62}$, $-N(R^8)SO_2R^7$ and $-OR^5$;
$R^4$ represents a straight- or branched-chain alkyl group containing up to 4 carbon atoms;
$R^6$, $R^{61}$ and $R^{62}$ which may be the same or different, each represents a straight- or branched-chain alkyl group containing up to 4 carbon atoms;
$R^7$ represents a straight- or branched-chain alkyl group containing up to 4 carbon atoms;
$R^8$ represents a straight- or branched-chain alkyl group containing up to 4 carbon atoms which is optionally substituted by one or more halogen atoms;
$R^9$ and $R^{10}$, which may be the same or different, each represents:
  the hydrogen atom; or
  a straight- or branched-chain alkyl group containing up to 4 carbon atoms which is optionally substituted by one or more halogen atoms.

A further preferred class of compounds of formula (I) are those wherein:
$R^1$ is methyl, isopropyl or cyclopropyl;
$R^2$ represents:
  a halogen atom;
  a straight- or branched-chain alkyl group containing up to 4 carbon atoms which is optionally substituted by one or more halogen atoms;
  a straight- or branched-chain alkyl group containing up to 4 carbon atoms which is substituted by one or more groups $-OR^5$; or
  a group selected from $-CO_2R^5$, $-S(O)_pR^6$, $-NR^{61}R^{62}$ and $-OR^5$;
$R^4$ represents a straight- or branched-chain alkyl group containing up to 4 carbon atoms;
$R^5$, $R^6$, $R^{61}$ and $R^{62}$ which may be the same or different, each represents a straight- or branched-chain alkyl group containing up to 4 carbon atoms which is optionally substituted by one or more halogen atoms;
$R^7$ represents a straight- or branched-chain alkyl group containing up to 4 carbon atoms;
$R^9$ and $R^{10}$, which may be the same or different, each represents:
  the hydrogen atom; or
  a straight- or branched-chain alkyl group containing up to 4 carbon atoms which is optionally substituted by one or more halogen atoms; and
t represents one.

In a further preferred embodiment where n is greater than zero the benzoyl ring of the compounds of formula (I) is 2,4-disubstituted or 2,3,4-trisubstituted. Compounds of formula (I) in which n is greater than zero and the benzoyl ring of the compound of formula (I) is 2,3-disubstituted are also preferred.

A further preferred class of compounds of formula (I) are those wherein:
R represents hydrogen or $-CO_2Et$;
$R^1$ represents cyclopropyl;
$R^2$ represents:
  a halogen atom or a group selected from $-CF_3$, $-S(O)_pMe$ and $-OMe$;

X represents —CHR$^9$—;

R$^3$ represents —S(O)$_q$R$^7$;

n represents zero, one or two;

R$^7$ represents:
  a straight- or branched-chain alkyl or alkenyl group containing up to four carbon atoms optionally substituted by from one to three fluorine atoms;
  or phenyl;

R$^9$ represents hydrogen or methyl; and p and q, which may be the same or different, each represents zero, one or two.

Particularly important compounds of formula (I) include the following:

1. 4-[4-bromo-2-(methylsulphenylmethyl)benzoyl]-5-cyclopropylisoxazole;
2. 4-[4-bromo-2-(methylsulphonylmethyl)benzoyl]-5-cyclopropylisoxazole;
3. 4-[4-chloro-2-methylsulphenyl-3-(methylsulphenylmethyl)benzoyl]-5-cyclopropylisoxazole;
4. 4-[4-chloro-3-(methylsulphenylmethyl)benzoyl]-5-cyclopropylisoxazole;
5. 4-[4-chloro-2-(methylsulphenylmethyl)benzoyl]-5-cyclopropylisoxazole;
6. 4-[4-bromo-2-(ethylsulphenylmethyl)benzoyl]-5-cyclopropylisoxazole;
7. 5-cyclopropyl-4-[2-methylsulphenylmethyl-4-(trifluoromethyl)benzoyl]isoxazole;
8. 5-cyclopropyl-4-[2-(methylsulphenylmethyl)benzoyl]isoxazole;
9. 5-cyclopropyl-4-[4-methylsulphenyl-2-(methylsulphenylmethyl)benzoyl]isoxazole;
10. 4-[4-bromo-2-(n-propylsulphenylmethyl)benzoyl]-5-cyclopropylisoxazole;
11. 4-[4-bromo-2-(isopropylsulphenylmethyl)benzoyl]-5-cyclopropylisoxazole;
12. 4-[2-(ethylsulphenylmethyl)benzoyl]-5-cyclopropylisoxazole;
13. 5-cyclopropyl-4-[4-fluoro-2-(methylsulphenylmethyl)benzoyl] isoxazole;
14. 4-{4-bromo-2-[(2-propenyl)sulphenylmethyl]benzoyl}-5-cyclopropylisoxazole;
15. 5-cyclopropyl-4-[3-fluoro-4-methoxy-2-(methylsulphenylmethyl)benzoyl]isoxazole;
16. 4-{4-bromo-2-[(2,2,2-trifluoroethyl)sulphenylmethyl]benzoyl}-5-cyclopropylisoxazole;
17. 4-[4-bromo-2-(t-butylsulphenylmethyl)benzoyl]-5-cyclopropylisoxazole;
18. 4-[4-bromo-2-(phenylsulphenylmethyl)benzoyl]-5-cyclopropylisoxazole;
19. 4-[2-chloro-4-(methylsulphenylmethyl)benzoyl]-5-cyclopropylisoxazole;
20. 5-cyclopropyl-4-[2-fluoro-4-(methylsulphenylmethyl)benzoyl]isoxazole;
21. 4-[2-bromo-4-(methylsulphenylmethyl)benzoyl]-5-cyclopropylisoxazole;
22. 5-cyclopropyl-4-[2-methoxy-4-(methylsulphenylmethyl)benzoyl]isoxazole;
23. 5-cyclopropyl-4-[2-methylsulphenyl-4-(methylsulphenylmethyl)benzoyl]isoxazole;
24. 5-cyclopropyl-4-[3,4-dichloro-2-(methylsulphenylmethyl)benzoyl]isoxazole;
25. 4-[3-chloro-4-methylsulphenyl-2-(methylsulphenylmethyl)benzoyl]-5-cyclopropylisoxazole;
26. 5-cyclopropyl-4-[3,4-dichloro-2-(1-methylsulphenyl)ethyl]benzoylisoxazole;
27. 5-cyclopropyl-4-[3,4-dichloro-2-(ethylsulphenylmethyl)benzoyl]isoxazole;
28. 4-[3-bromo-2-(methylsulphenylmethyl)benzoyl]-5-cyclopropylisoxazole;
29. 4-[4-chloro-3-fluoro-2-(methylsulphenylmethyl)benzoyl]-5-cyclopropylisoxazole;
30. 4-[3-bromo-4-chloro-2-(methylsulphenylmethyl)benzoyl]-5-cyclopropylisoxazole;
31. 4-[4-chloro-2-methoxy-3-(methylsulphenylmethyl)benzoyl] -5-cyclopropylisoxazole;
32. 5-cyclopropyl-4-[2,4-dichloro-3-(methylsulphenylmethyl)benzoyl]isoxazole;
33. 4-[2-chloro-4-methylsulphenyl-3-(methylsulphenylmethyl)benzoyl]-5-cyclopropylisoxazole;
34. 4-[4-chloro-3-methylsulphenyl-2-(methylsulphenylmethyl)benzoyl]-5-cyclopropylisoxazole;
35. 5-cyclopropyl-4-[3,4-dichloro-2-(methylsulphinylmethyl)benzoyl]isoxazole;
36. 4-[3-chloro-4-methylsulphenyl-2-(methylsulphinylmethyl)benzoyl]-5-cyclopropylisoxazole;
37. 4-[4-bromo-2-(methylsulphinylmethyl)benzoyl]-5-cyclopropylisoxazole;
38. 5-cyclopropyl-4-{3,4-dichloro-2-[1-(methylsulphinyl)ethyl]benzoyl}isoxazole;
39. 4-[4-chloro-2-(methylsulphinylmethyl)benzoyl]-5-cyclopropylisoxazole;
40. 4-[4-chloro-2-(methylsulphonylmethyl)benzoyl]-5-cyclopropylisoxazole;
41. 4-[4-bromo-2-(ethylsulphinylmethyl)benzoyl]-5-cyclopropylisoxazole;
42. 4-[4-bromo-2-(ethylsulphonylmethyl)benzoyl]-5-cyclopropylisoxazole;
43. 5-cyclopropyl-4-[2-methylsulphinylmethyl-4-(trifluoromethyl)benzoyl]isoxazole;
44. 5-cyclopropyl-4-[2-methylsulphonylmethyl-4-(trifluoromethyl)benzoyl]isoxazole;
45. 5-cyclopropyl-4-[4-methylsulphenyl-2-(methylsulphinylmethyl)benzoyl]isoxazole;
46. 5-cyclopropyl-4-[4-methylsulphonyl-2-(methylsulphonylmethyl)benzoyl]isoxazole;
47. 5-cyclopropyl-4-[2-(methylsulphinylmethyl)benzoyl]isoxazole;
48. 5-cyclopropyl-4-[2-(methylsulphonylmethyl)benzoyl]isoxazole;
49. 5-cyclopropyl-4-[3,4-dichloro-2-(ethylsulphonylmethyl)benzoyl] isoxazole;
50. 5-cyclopropyl-4-[3,4-dichloro-2-(ethylsulphinylmethyl)benzoyl]isoxazole;
51. 4-[4-bromo-2-(n-propylsulphinylmethyl)benzoyl]-5-cyclopropylisoxazole;
52. 4-[4-bromo-2-(n-propylsulphonylmethyl)benzoyl]-5-cyclopropylisoxazole;
53. 4-[bromo-2-(isopropylsulphinylmethyl)benzoyl]-5-cyclopropylisoxazole;
54. 4-[4-bromo-2-(isopropylsulphonylmethyl)benzoyl]-5-cyclopropylisoxazole;
55. ethyl 4-[4-bromo-2-(methylsulphinylmethyl)benzoyl]-5-cyclopropylisoxazole-3-carboxylate;
56. ethyl 4-[4-bromo-2-(methylsulphonylmethyl)benzoyl]-5-cyclopropylisoxazole-3-carboxylate;
57. 4-[3-bromo-2-(methylsulphinylmethyl)benzoyl]-5-cyclopropylisoxazole;
58. 4-[3-bromo-2-(methylsulphonylmethyl)benzoyl]-5-cyclopropylisoxazole;
59. ethyl 4-[3-bromo-2-(methylsulphonylmethyl)benzoyl]-5-cyclopropylisoxazole-3-carboxylate;
60. ethyl 4-[3-bromo-2-(methylsulphinylmethyl)benzoyl]-5-cyclopropylisoxazole-3-carboxylate;

61. 4-[3-bromo-4-chloro-2-(methylsulphinylmethyl)benzoyl]-5-cyclopropylisoxazole;
62. 4-[3-bromo-4-chloro-2-(methylsulphonylmethyl)benzoyl]-5-cyclopropylisoxazole;
63. 4-[4-chloro-3-fluoro-2-(methylsulphinylmethyl)benzoyl]-5-cyclopropylisoxazole;
64. 4-{4-bromo-2-[(2,2,2-trifluoroethyl)sulphonylmethyl]benzoyl}-5-cyclopropylisoxazole;
65. 4-{4-bromo-2-[(2-propenyl)sulphonylmethyl]benzoyl}-5-cyclopropylisoxazole;
66. 4-{4-bromo-2-[(2-propenyl)sulphinylmethyl]benzoyl}-5-cyclopropylisoxazole;
67. 4-{4-bromo-2-[(1-propenyl)sulphinylmethyl]benzoyl}-5-cyclopropylisoxazole;
68. 4-[4-chloro-3-methylsulphenyl-2-(methylsulphinylmethyl)benzoyl]-5-cyclopropylisoxazole;
69. 4-[4-chloro-3-methylsulphonyl-2-(methylsulphonylmethyl)benzoyl)]-5-cyclopropylisoxazole;
70. 4-[4-bromo-2-(t-butylsulphonylmethyl)benzoyl]-5-cyclopropylisoxazole;
71. 4-[4-bromo-2-(phenylsulphonylmethyl)benzoyl]-5-cyclopropylisoxazole;
72. 5-cyclopropyl-4-[2-(ethylsulphinylmethyl)benzoyl]isoxazole;
73. 5-cyclopropyl-4-[2-(ethylsulphonylmethyl)benzoyl]isoxazole;
74. 5-cyclopropyl-4-[3-fluoro-4-methoxy-2-(methylsulphonylmethyl)benzoyl]isoxazole;
75. 4-[4-chloro-3-methylsulphinylmethyl-2-(methoxy)benzoyl]-5-cyclopropylisoxazole;
76. 5-cyclopropyl-4-[2,4-dichloro-3-(methylsulphinylmethyl)benzoyl]isoxazole;
77. 4-[2-chloro-4-(methylsulphinylmethyl)benzoyl]-5-cyclopropylisoxazole;
78. 4-[2-chloro-4-(methylsulphonylmethyl)benzoyl]-5-cyclopropylisoxazole;
79. 5-cyclopropyl-4-[2-fluoro-4-(methylsulphonylmethyl)benzoyl]isoxazole;
80. 4-[2-bromo-4-(methylsulphinylmethyl)benzoyl]-5-cyclopropylisoxazole;
81. 4-[2-bromo-4-(methylsulphonylmethyl)benzoyl]-5-cyclopropylisoxazole;
82. 5-cyclopropyl-4-[2-methoxy-4-(methylsulphonylmethyl)benzoyl]isoxazole;
83. 5-cyclopropyl-4-[2-methylsulphenyl-4-(methylsulphinylmethyl)benzoyl]isoxazole;
84. 4-[3-chloro-4-methylsulphonyl-2-(methylsulphonylmethyl)benzoyl]-5-cyclopropylisoxazole;
85. 5-cyclopropyl-4-[3,4-dichloro-2-(methylsulphonylmethyl)benzoyl]isoxazole;
86. 4-[4-chloro-2-methoxy-3-(methylsulphonylmethyl)benzoyl]-5-cyclopropylisoxazole;
87. 5-cyclopropyl-4-[2,4-dichloro-3-(methylsulphonylmethyl)benzoyl]isoxazole;
88. ethyl 4-[4-bromo-2-(methylsulphenylmethyl)benzoyl]-5-cyclopropylisoxazole-3-carboxylate;
89. ethyl 4-[3-bromo-2-(methylsulphenylmethyl)benzoyl]-5-cyclopropylisoxazole-3-carboxylate;
90. 4-[4-chloro-3-ethylsulphenylmethyl-2-(methylsulphenyl)-benzoyl]-5-cyclopropylisoxazole.

The numbers 1 to 90 are assigned to these compounds for reference and identification hereafter.

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) in which R represents hydrogen may be prepared by the reaction of a compound of formula (II):

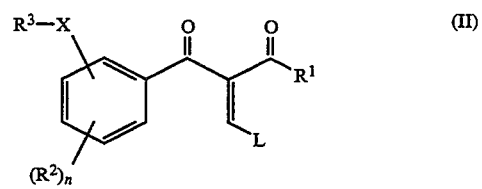

wherein L is a leaving group and $R^1$, $R^2$, $R^3$, n and X are as hereinbefore defined, with hydroxylamine or a salt of hydroxylamine. Hydroxylamine hydrochloride is generally preferred. Generally L is alkoxy, for example ethoxy, or N,N-dialkylamino, for example dimethylamino. The reaction is generally carried out in an organic solvent such as ethanol or acetonitrile or a mixture of a water-miscible organic solvent and water, preferably in a ratio of organic solvent:water of from 1:99 to 99:1, optionally in the presence of a base or acid acceptor such as triethylamine or sodium acetate at a temperature from 0° to 100° C.

According to a further feature of the present invention compounds of formula (I) in which R represents hydrogen may be prepared by the reaction of a compound of formula (III):

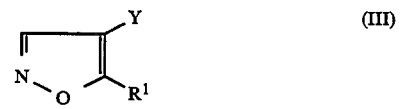

wherein $R^1$ is as hereinbefore defined and Y represents a carboxyl group or a reactive derivative thereof (such as a carboxylic acid chloride or carboxylic ester), or a cyano group, with an appropriate organometallic reagent such as a Grignard reagent or an organolithium reagent. The reaction is generally carried out in an inert solvent such as ether or tetrahydrofuran at a temperature from 0° C. to the reflux temperature of the mixture.

According to a further feature of the present invention compounds of formula (I) wherein R represents a group —$CO_2R^4$, q represents 0 or 2 and $R^2$ represents a group $R^{21}$ which is as hereinbefore defined for $R^2$ provided that p is 0 or 2, may be prepared by the reaction of a compound of formula (IV):

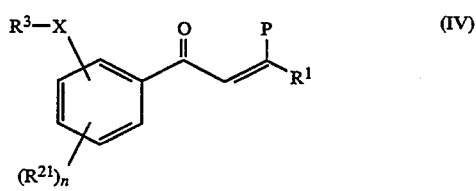

wherein $R^1$, $R^{21}$, $R^3$, X and n are as hereinbefore defined, q is 0 or 2 and P is a leaving group such as N,N-dialkylamino, with a compound of formula $R^4O_2CC(Z)=NOH$ wherein $R^4$ is as hereinbefore defined and Z is a halogen atom. Generally Z is chlorine or bromine. The reaction is generally performed in an inert solvent such as toluene or dichloromethane either in the presence of a base such as triethylamine or a catalyst such as a 4 Angstrom molecular sieve or fluoride ion.

According to a further feature of the present invention compounds of formula I in which R represents a group $-CO_2R^4$, q represents 0 or 2 and $R^2$ represents a group $R^{21}$ as hereinbefore defined, may be prepared by the reaction of a compound of formula (V):

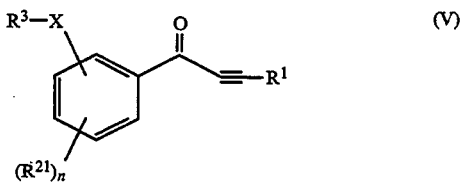

wherein $R^1$, $R^{21}$, $R^3$, X and n are as hereinbefore defined and q represents 0 or 2, with a compound of formula $R^4O_2CC(Z)=NOH$, wherein Z and $R^4$ are as hereinbefore defined. The reaction is generally performed in an inert solvent such as toluene or dichloromethane optionally in the presence of a base such as triethylamine or a catalyst such as a 4 Angstrom molecular sieve or fluoride ion. The reaction can be carried out at a temperature between room temperature and the reflux temperature of the mixture.

According to a further feature of the present invention compounds of formula (I) wherein R represents $-CO_2R^4$, q represents 0 or 2 and $R^2$ represents a group $R^{21}$ as hereinbefore defined, may be prepared by the reaction of a salt of a compound of formula (VI):

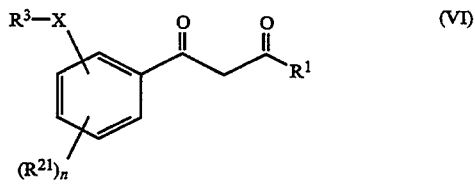

wherein $R^1$, $R^{21}$, $R^3$, X and n are as hereinbefore defined and q represents 0 or 2, with a compound of formula $R^4O_2CC(Z)=NOH$, wherein $R^4$ and Z are as hereinbefore defined. Preferred salts include sodium or magnesium salts. The reaction may be performed in an inert solvent such as dichloromethane or acetonitrile at a temperature between room temperature and the reflux temperature of the mixture.

Intermediates in the preparation of compounds of formula (I) may be prepared by the application or adaptation of known methods.

Compounds of formula (II) in which L represents alkoxy or N,N-dialkylamino may be prepared by the reaction of a compound of formula (VI) with either a trialkyl orthoformate such as triethyl orthoformate or a N,N-dimethylformamide dialkyl acetal such as N,N-dimethylformamide dimethyl acetal.

The reaction with triethyl orthoformate can be carried out in the presence of acetic anhydride at the reflux temperature of the mixture and the reaction with di-methylformamide dialkyl acetal is carried out optionally in the presence of an inert solvent at a temperature from room temperature to the reflux temperature of the mixture.

Compounds of formula (IV) may be prepared by the reaction of a compound of formula (VII) with a benzoyl chloride of formula (VIII):

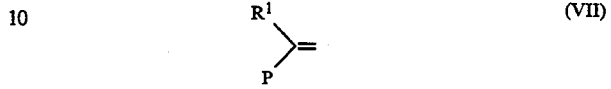

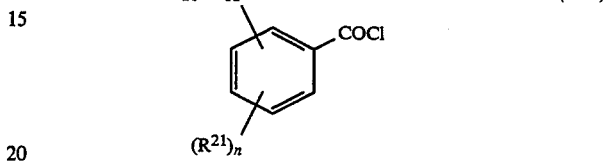

wherein $R^1$, $R^{21}$, $R^3$, X, n and P are as hereinbefore defined provided that the group $-XR^3$ is not ortho to the carboxyl group, and q represents 0 or 2. The reaction is generally carried out in the presence of an organic base such as triethylamine in an inert solvent such as toluene or dichloromethane at a temperature between $-20°$ C. and room temperature.

Compounds of formula (V) may be prepared by the metallation of an acetylene of formula (IX):

$$R^1C{\equiv}CH \qquad (IX)$$

wherein $R^1$ is as hereinbefore defined, followed by reaction of the metal salt thus obtained with a benzoyl chloride of formula (VIII). The metallation is generally performed using n-butyl lithium in an inert solvent such as ether or tetrahydrofuran at a temperature from $-78°$ C. to $0°$ C. The subsequent reaction with the benzoyl chloride is carried out in the same solvent at a temperature between $-78°$ C. and room temperature.

Compounds of formula (VI) may be prepared by the reaction of an acid chloride of formula (VIII) with the metal salt of a compound of formula (X):

wherein $R^1$ is as hereinbefore defined, to give a compound of formula (XI):

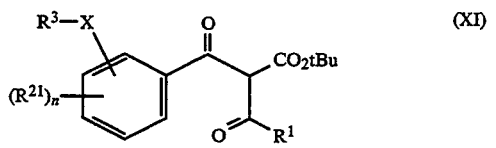

wherein $R^1$, $R^{21}$ $R^3$, X and n are as hereinbefore defined and q is 0 or 2, which is subsequently decarboxylated to give a compound of formula (VI). The reaction to produce the metal salt of a compound of formula (X) is generally performed in a solvent such as a lower alcohol, preferably methanol. Preferably the metal is magnesium. The metal salt of the compound of formula (X) is subsequently reacted with an acid chloride of formula (VIII) in an inert solvent such as toluene or acetonitrile.

The decarboxylation is generally performed by refluxing the compound of formula (XI) in the presence of a catalyst, such as para-toluenesulphonic acid, in an inert solvent e.g. toluene.

Compounds of formula (VI) may also be prepared by the reaction of a benzoic acid ester of formula (XII):

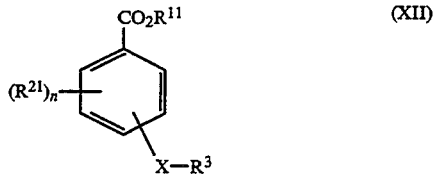

wherein $R^{21}$, $R^3$, X and n are as hereinbefore defined, q is 0 or 2 and $R^{11}$ represents a lower alkyl group, with a compound of formula (XIII):

wherein $R^1$ is as hereinbefore defined. The reaction is generally performed in a solvent such as diethyl ether, tetrahydrofuran or N,N-dimethylformamide, in the presence of a base, preferably an alkali metal base such as sodium hydride, at a temperature from 0° C. to reflux temperature.

Acid chlorides of formula (VIII) in which the group $-XR^3$ is not ortho to the carboxyl group may be prepared by the reaction of a benzoic acid of formula (XIV):

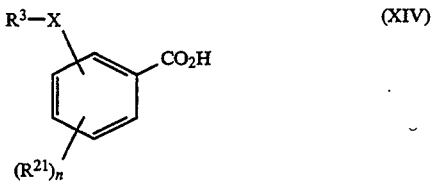

wherein $R^{21}$, $R^3$, X and n are as hereinbefore defined and q is 0 or 2, and the group $-XR^3$ is not ortho to the carboxyl group, with a chlorinating agent, for example thionyl chloride at the reflux temperature of the mixture. A number of the benzoic acids of formula (XIV) are novel and as such constitute a further feature of the present invention. In particular compounds of formula (XIV) in which $-XR^3$ is in the 2-position of the benzoic acid, $-XR^3$ is $-CH_2S(O)_qR^7$; $(R^{21})_n$ is selected from 3,4-dihalogen, 3-halogen, 3-SMe-4-halogen, 3-SMe, 4-bromo, 4-fluoro, 4-$CF_3$ and 4-$OCF_3$; q is 0, 1 or 2 and $R^7$ represents straight- or branched-chain alkyl or haloalkyl containing up to 3 carbon atoms, are preferred. Compounds of formula (XIV) in which $-XR^3$ is in the 3-position of the benzoic acid, $-XR^3$ is $-CH_2S(O)_qR^7$; $(R^{21})_n$ is 4-halogen-2-(-SMe, -OMe or -halogen); q is 0, 1 or 2 and $R^7$ represents straight- or branched-chain alkyl or haloalkyl containing up to 3 carbon atoms, are also preferred.

Compounds of formula (XII) in which $-XR^3$ represents $-CH_2SR^7$ and one of the groups $R^{21}$ is an unsubstituted amino group which is ortho to the group $-XR^3$ may be prepared by the reaction of the corresponding compound of formula (XII) in which $-XR^3$ is replaced by a hydrogen atom, with a chlorinating agent, preferably N-chlorosuccinimide or t-butyl hypochlorite, followed by reaction with a sulphide of formula MeS-$R^7$ and a base, preferably triethylamine or sodium alkoxide (e.g. sodium methoxide), in an inert solvent such as dichloromethane at a temperature from $-78°$ C. to 50° C. The reaction is particularly useful for preparing compounds of formula (XII) in which $-XR^3$ represents $-CH_2SMe$ and is described in the literature (e.g. Gassman et al J. American Chem. Soc., Vol. 95, page 588, 1973). The unsubstituted amino group may be converted into other groups $R^{21}$ using standard diazotisation chemistry.

Compounds of formula (XII) in which $-XR^3$ represents $-XSR^7$ may be prepared by the reaction of the corresponding compound of formula (XII) in which $-XSR^7$ is replaced by $-XL$ wherein L is a leaving group (preferably bromine or chlorine) with a thiol of formula HS$R^7$ or preferably a salt thereof (such as the sodium or potassium salt). The reaction may optionally be performed in the presence of an iodide such as sodium, potassium or tetraalkylammonium iodide, and the salt of the thiol HS$R^7$ may be either pre-formed or generated in situ from the parent thiol by treatment with base (e.g. sodium or potassium carbonate, sodium hydride or a sodium alkoxide).

Intermediates of formulae (III), (VII), (IX), (X), (XII) and (XIII) are known or may be prepared by the application or adaptation of known methods.

Those skilled in the art will appreciate that some compounds of formula (I) may be prepared by the interconversion of other compounds of formula (I) and such interconversions constitute yet more features of the present invention. Examples of such interconversions are hereafter described.

According to a further feature of the present invention compounds in which p is one or two and/or q is one or two may be prepared by the oxidation of the sulphur atom of the corresponding compounds in which p and/or q is zero or one. The oxidation of the sulphur atom is generally carried out using for example 3-chloroperoxybenzoic acid in an inert solvent such as dichloromethane at a temperature from $-40°$ C. to room temperature, or hydrogen peroxide in acetic acid in the presence of acetic anhydride or concentrated sulphuric acid, or using potassium peroxymonosulphate as the oxidising agent.

The following examples illustrate the preparation of compounds of formula (I) and the following reference examples illustrate the preparation of intermediates of the invention. In the present specification b.p. means boiling point; m.p. means melting point; cPr represents cyclopropyl.

EXAMPLE 1

A mixture of 1-(4-bromo-2-methylsulphenylmethylphenyl)-3-cyclopropyl-2-N,N-dimethylaminomethylene propan-1,3-dione (2 g) and hydroxylamine hydrochloride (0.45 g) in ethanol was stirred at room temperature for one hour. The reaction mixture was then poured onto water, extracted with ether and dried (anhydrous sodium sulphate). Evaporation of the solvent gave a brown gum which was purified by column chromatography on silica gel to yield 4-[4-bromo-2-(methylsulphenylmethyl)benzoyl]-5 -cyclopropylisoxazole (compound 1, 1.22 g), NMR (CDCl$_3$): 1.22 (2H,m), 1.47 (2H,m), 2.00 (3H,s), 2.69 (1H,m), 3.85 (2H,s), 7.29 (1H,m), 7.50 (1H,m), 7.59 (1H,m), 8.20 (1H,s).

By proceeding in a similar manner the following compounds of formula I were prepared from the appropriate starting materials.

| Cpd | R | R¹ | XR³ | (R²)ₙ | m.p.(°C.)/NMR |
|-----|---|----|----|------|--------------|
| 5 | H | cPr | 2-CH₂SMe | 4-Cl | 87–89.5 |
| 6 | H | cPr | 2-CH₂SEt | 4-Br | (a) |
| 7 | H | cPr | 2-CH₂SMe | 4-CF₃ | 58.5–60.5 |
| 8 | H | cPr | 2-CH₂SMe | — | (b) |
| 9 | H | cPr | 2-CH₂SMe | 4-SMe | (c) |
| 10 | H | cPr | 2-CH₂S-n-Pr | 4-Br | (d) |
| 11 | H | cPr | 2-CH₂S-i-Pr | 4-Br | 74.5–78 |
| 12 | H | cPr | 2-CH₂SEt | — | (e) |
| 13 | H | cPr | 2-CH₂SMe | 4-F | (f) |
| 14 | H | cPr | 2-CH₂SCH₂CH=CH₂ | 4-Br | (g) |
| 15 | H | cPr | 2-CH₂SMe | 3-F-4-OMe | 87.5–89.5 |
| 16 | H | cPr | 2-CH₂SCH₂CF₃ | 4-Br | (h) |
| 17 | H | cPr | 2-CH₂S-t-Bu | 4-Br | 86–87 |
| 18 | H | cPr | 2-CH₂S-Ph | 4-Br | (i) |
| 19 | H | cPr | 4-CH₂SMe | 2-Cl | 58–61 |
| 20 | H | cPr | 4-CH₂SMe | 2-F | (j) |
| 21 | H | cPr | 4-CH₂SMe | 2-Br | (k) |
| 22 | H | cPr | 4-CH₂SMe | 2-OMe | (l) |
| 23 | H | cPr | 4-CH₂SMe | 2-SMe | (m) |

NMR (CDCl₃ unless otherwise stated)
(a) 1.0(t,3H), 15.0(m,2H), 1.2(m2H), 2.35(q,3H), 2.5(m,1H), 3.75(s,2H), 7.15(d,1H), 7.35(d,1H), 7.5(s,1H), 8.05(s,1H).
(b) 1.11(m,2H), 1.25(m,2H), 1.9(5,3H), 25(m,1H), 3.82(s,2H), 7.33(m,4H), 8.17(s,1H).
(c) 1.25(m,2H), 1.4(m,2H), 2.0(s,3H), 2.5(s,3H), 2.65(m,1H), 3.9(s,2H), 7.15(d,1H), 7.25(s,1H), 7.35(d,1H), 8.25(s,1H).
(d) 0.95(t,3H), 1.3(m,2H), 1.4(m,2H), 1.55(m,2H), 2.4(t,2H), 2.6(m,1H), 3.9(s,2H), 7.25(d,1H), 7.45(d,1H), 7.55(s,1H), 8.2(s,1H).
(e) 1.12(m,5H), 1.27(m,2H), 23(q,2H), 2.51(m,1H), 3.88(s,2H), 7.28(m,4H), 8.17(s,1H).
(f) 1.13(m,2H), 1.25(m,2H), 1.92(s,3H), 2.5(m,1H), 3.8(s,2H), 6.96(m,1H), 7.1(dd,1H), 7.33(dd,1H), 8.13(s,1H).
(g) 1.25(m,2H), 1.35(m,2H), 2.6(m,1H), 3.0(d,2H), 3.8(s,2H), 5.1(dd,2H), 5.7(m,1H), 7.3(d,1H), 7.45(d,1H), 7.55(s,1H), 8.2(s,1H).
(h) 1.2(m,2H), 1.3(m,2H), 2.55(m,1H), 2.95(q,2H), 3.95(s,2H), 7.25(d,1H), 7.45(d,1H), 7.5(s,1H), 8.1(s,1H).
(i) 1.35(m,2H), 1.45(m,2H), 2.55(m,1H), 4.3(s,2H), 7.2(d,1H), 7.25(m,5H), 7.5(d,1H), 7.6(s,1H), 8.15(s,1H).
(j) 1.25(m,2H), 1.35(m,2H), 2.0(s,3H), 2.8(m,1H), 3.7(s,2H), 7.1–7.3(m,2H), 7.55(t,1H), 8.3(s,1H).
(k) 1.2(m,2H), 1.35(m,2H), 2.0(s,3H), 2.6(m,1H), 3.65(s,2H), 7.2–7.4(m,2H), 7.6(s,1H), 8.15(s,1H).
(l) 1.2(m,2H), 1.3(m,2H), 2.0(s,3H), 2.75(m,1H), 3.65(s,2H), 3.8(s,3H), 6.95(m,2H), 7.4(d,1H), 8.2(s,1H).
(m) 1.2(m,2H), 1.35(m,2H), 2.0(brs,3H), 2.5(s,3H), 2.7(m,1H), 3.7(brs, 2H), 7.1(d,1H), 7.3(s,1H), 7.45(d,1H), 8.2(s,1H).

EXAMPLE 2

A mixture of 1-[4-chloro-3-(methylsulphenylmethyl)-2-(methylsulphenyl)phenyl]-2-ethoxymethylene-3-cyclopropylpropan-1,3-dione (2.3 g), hydroxylamine hydrochloride (0.52 g) and sodium acetate (0.46 g) in ethanol was stirred at room temperature overnight. The resulting mixture was filtered and the solid collected, washed with water and air dried to yield 4-[4-chloro-2-(methylsulphenyl)-3-(methylsulphenylmethyl)benzoyl]-5-cyclopropylisoxazole (Compound 3, 0.46 g) as a yellow solid, m.p. 79.9°–80.5° C.

By proceeding in a similar manner compound 4 was prepared. NMR (CDCl₃) 1.3 (2H,m), 1.4 (2H,m), 2.1 (3H,s), 2.75 (1H,m), 3.85 (2H,m), 7.55 (1H,d), 7.65 (1H,m), 7.8 (1H,d), 8.4 (1H,s).

By proceeding in a similar manner the following compounds of formula I were also prepared from the appropriate starting materials.

| Cpd | R | R¹ | XR³ | (R²)ₙ | m.p.(°C.)/NMR |
|-----|---|----|----|------|--------------|
| 34 | H | cPr | 2-CH₂SMe | 3-SMe-4-Cl | (a) |
| 25 | H | cPr | 2-CH₂SMe | 3-Cl-4-SMe | 127–131 |
| 29 | H | cPr | 2-CH₂SMe | 3-F-Cl | (b) |
| 31 | H | cPr | 3-CH₂SMe | 2-OMe-4-Cl | 68–69 |
| 32 | H | cPr | 3-CH₂SMe | 2,4-Cl₂ | (c) |
| 24 | H | cPr | 2-CH₂SMe | 3,4-Cl₂ | (d) |
| 30 | H | cPr | 2-CH₂SMe | 3-Br-4-Cl | (e) |
| 33 | H | cPr | 3-CH₂SMe | 2-Cl-4-SMe | (f) |
| 28 | H | cPr | 2-CH₂SMe | 3-Br | (g) |
| 27 | H | cPr | 2-CH₂SEt | 3,4-Cl₂ | 77.5–8.0 |
| 26 | H | cPr | 2-CH₂(Me)SMe | 3,4-Cl₂ | (h) |
| 90 | H | cPr | 3-CH₂SEt | 2-SMe-4Cl | (i) |

NMR (CDCl₃ unless otherwise stated)
(a) 1.25(m,4H), 2.0(s,3H), 2.4(s,3H), 2.6(m,1H), 4.3(s,2H), 7.3(dd,2H), 8.2(s,1H).
(b) 1.2(m,4H), 1.95(s,3H), 2.4(s,3H), 2.6(m,1H), 4.3(s,2H), 7.3(dd,2H), 8.2(s,1H).
(c) 1.2(m,4H), 2.2(s,3H), 2.6(m,1H), 4.05(s,2H), 7.3(dd,2H), 8.15(s,1H).
(d) 1.2(m,4H), 1.9(s,3H), 2.5(m,1H), 4.0(s,2H),7.25(dd,2H), 8.1(m,1H).
(e) 1.2–1.45(m,4H), 2.05(s,3H), 2.6(m,1H), 4.2(s,2H), 7.25(d,1H), 7.45(d,1H), 8.2(s,1H).
(f) 1.25(m,4H), 2.15(s,3H), 2.55(s,3H), 2.6(m,1H), 4.05(s,2H), 7.2(dd,2H), 8.15(s,1H).
(g) 1.1–1.4(m,4H), 2.05(s,3H), 2.6(m,1H), 4.1(s,2H), 7.2(dd,1H), 7.3(d,1H), 7.7(d,1H), 8.2(s,1H).
(h) 1.1–1.4(m,4H), 1.67(d,3H), 1.9(s,3H), 2.6(m,1H), 4.4(q,1H), 7.05(d,1H), 7.4(d,1H), 8.05(s,1H).
(i) 1.3(m,4H), 1.4(t,3H), 2.3(s,3H), 2.7(m,1H), 4.3(s,2H), 7.15(d,1H), 7.4(d,1H), 8.1(s,1H).

EXAMPLE 3

A mixture of 4-[4-bromo-2-(methylsulphenylmethyl)-benzoyl]-5-cyclopropylisoxazole (0.7 g) and 3-chloroperbenzoic acid (1.5 g) in dichloromethane was stirred for 30 minutes at 0° C. and then at 1 hour at 25° C. The mixture was then treated with an aqueous solution of sodium bisulphite and filtered. After decanting, the organic layer was washed with a solution of sodium acetate, brine, dried (sodium sulphate), filtered and evaporated to yield a clean oil which was crystallised from ether to give 5-cyclopropyl-4-[4-bromo-2-(methylsulphonylmethyl)benzoyl]isoxazole (compound 2, 0.61 g) as a white solid, m.p. 154.2° C.

By proceeding in a similar manner the following compounds of formula (I) above were prepared from the appropriate starting materials.

| Cpd | R | R¹ | XR³ | (R²)ₙ | m.p.(°C.)/NMR |
|-----|---|----|----|------|--------------|
| 35 | H | cPr | 2-CH₂SOMe | 3,4-Cl₂ | 53–54 |
| 36 | H | cPr | 2-CH₂SOMe | 3-Cl-4-SMe | 68–70 |
| 37 | H | cPr | 2-CH₂SOMe | 4-Br | 125.5–131.5 |
| 38 | H | cPr | 2-CH₂(Me)SOMe | 3,4-Cl₂ | 46–50 |
| 39 | H | cPr | 2-CH₂SOMe | 4-Cl | 94–97.5 |
| 40 | H | cPr | 2-CH₂SO₂Me | 4-Cl | 156–157.5 |
| 41 | H | cPr | 2-CH₂SOEt | 4-Br | (a) |
| 42 | H | cPr | 2-CH₂SO₂Et | 4-Br | 110–113.5 |
| 43 | H | cPr | 2-CH₂SOMe | 4-CF₃ | 109–110 |
| 45 | H | cPr | 2-CH₂SOMe | 4-SMe | 97.5–99 |
| 46 | H | cPr | 2-CH₂SO₂Me | 4-SO₂Me | 191–194 |
| 47 | H | cPr | 2-CH₂SOMe | — | 73–75 |

-continued

| | | | | | |
|---|---|---|---|---|---|
| 48 | H | cPr | 2-CH$_2$SO$_2$Me | — | 131.5–133.5 |
| 49 | H | cPr | 2-CH$_2$SO$_2$Et | 3,4-Cl$_2$ | 152.5–153.5 |
| 50 | H | cPr | 2-CH$_2$SOEt | 3,4-Cl$_2$ | 113–115 |
| 51 | H | cPr | 2-CH$_2$SO-n-Pr | 4-Br | 93–95 |
| 52 | H | cPr | 2-CH$_2$SO$_2$-n-Pr | 4-Br | 108–109 |
| 53 | H | cPr | 2-CH$_2$SO-i-Pr | 4-Br | 95–96 |
| 54 | H | cPr | 2-CH$_2$SO$_2$-i-Pr | 4-Br | 140.5–141 |
| 55 | CO$_2$Et | cPr | 2-CH$_2$SOMe | 4-Br | (b) |
| 56 | CO$_2$Et | cPr | 2-CH$_2$SO$_2$Me | 4-Br | 129–130.5 |
| 57 | H | cPr | 2-CH$_2$SOMe | 3-Br | 134.5–135.5 |
| 58 | H | cPr | 2-CH$_2$SO$_2$Me | 3-Br | 198–199 |
| 59 | CO$_2$Et | cPr | 2-CH$_2$SO$_2$Me | 3-Br | 134–135 |
| 60 | CO$_2$Et | cPr | 2-CH$_2$SOMe | 3-Br | (c) |
| 61 | H | cPr | 2-CH$_2$SOMe | 3-Br-4-Cl | (d) |
| 62 | H | cPr | 2-CH$_2$SO$_2$Me | 3-Br-4-Cl | 136–138 |
| 63 | H | cPr | 2-CH$_2$SOMe | 3-F-4-Cl | (e) |
| 64 | H | cPr | 2-CH$_2$SO$_2$CH$_2$CF$_3$ | 4-Br | 112–115 |
| 65 | H | cPr | 2-CH$_2$SO$_2$CH$_2$CH=CH$_2$ | 4-Br | (f) |
| 66 | H | cPr | 2-CH$_2$SOCH$_2$CH=CH$_2$ | 4-Br | (g) |
| 67 | H | cPr | 2-CH$_2$SOCH=CHCH$_3$ | 4-Br | (h) |
| 69 | H | cPr | 2-CH$_2$SO$_2$Me | 3-SO$_2$Me-4-Cl | 156–157.5 |
| 70 | H | cPr | 2-CH$_2$SO$_2$-t-Bu | 4-Br | 166–168 |
| 71 | H | cPr | 2-CH$_2$SO$_2$Ph | 4-Br | (i) |
| 72 | H | cPr | 2-CH$_2$SOEt | — | 87–89.5 |
| 73 | H | cPr | 2-CH$_2$SO$_2$Et | — | 140–141 |
| 74 | H | cPr | 3-CH$_2$SO$_2$Me | 3-F-4-OMe | 118.5–120 |
| 75 | H | cPr | 3-CH$_2$SOMe | 2-OMe-4-Cl | (j) |
| 76 | H | cPr | 4-CH$_2$SOMe | 2,4-Cl$_2$ | 107–108 |
| 77 | H | cPr | 4-CH$_2$SOMe | 2-Cl | (k) |
| 78 | H | cPr | 4-CH$_2$SO$_2$Me | 2-Cl | 139–142 |
| 79 | H | cPr | 4-CH$_2$SO$_2$Me | 2-F | 114–116.5 |
| 80 | H | cPr | 4-CH$_2$SOMe | 2-Br | (l) |
| 81 | H | cPr | 4-CH$_2$SO$_2$Me | 2-Br | 132–137 |
| 82 | H | cPr | 4-CH$_2$SO$_2$Me | 2-OMe | 44–48 |
| 83 | H | cPr | 2-CH$_2$SOMe | 2-SMe | (m) |
| 44 | H | cPr | 2-CH$_2$SO$_2$Me | 4-CF$_3$ | 107–108 |
| 68 | H | cPr | 2-CH$_2$SOMe | 3-SMe-4-Cl | (n) |

Compound 46 was prepared from appropriate sulphoxide, compound 45.
Compounds 65 and 66 were prepared from a mixture of the appropriate sulphides.
NMR (CDCl$_3$ unless otherwise stated)
(a) 1.2(m,2H), 1.35(m,2H), 1.35(t,3H), 2.6(m,1H), 2.73(m,2H), 3.95
(d,1H), 4.4(d,1H), 7.4(d,1H), 7.6(d,1H), 7.7(s,1H), 8.25(s,1H).
(b) 1.25(t,3H), 1.25(m,2H), 13.5(m,2H), 2.25(m,1H), 2.7(s,3H), 4.1
(q,2H), 4.2(d,1H), 4.55(d,1H), 7.4(d,1H), 7.55(d,1H), 7.7(s,1H).
(c) 1.0–1.4(m,4H), 1.25(t,3H), 2.3(m,1H), 2.7(s,3H), 4.2(q,4H),
4.7(d,1H), 4.8(d,1H), 7.25(dd,1H), 7.5(d,1H), 7.85(d,1H).
(d) 1.15–1.45(m,4H), 2.6(s,3H), 2.65(m,1H), 4.7(d,1H),
4.75(d,1H), 7.4(d,1H), 7.6(d,1H), 8.25(s,1H).
(e) 1.2(m,4H), 2.45(s,3H), 2.6(m,1H), 4.35(dq,2H), 7.3(m,2H), 8.15(s,1H).
(f) 1.2(m,2H), 1.35(m,2H), 2.5(m,1H), 3.76(d,2H), 4.55(s,2H), 5.45
(dd,2H), 5.85(m,1H), 7.4(d,1H), 7.6(d,1H), 7.65(s,1H), 8.25(s,1H).
(g) 1.25(m,2H), 1.4(m,2H), 2.6(m,1H), 3.5(m,2H), 4.0(d,1H), 4.45(d,1H),
5.45(dd,2H), 5.95(m,1H), 7.45(d,1H), 7.6(d,1H), 7.65(s,1H), 8.25(s,1H).
(h) 1.3(m,2H), 1.4(m,2H), 1.9(d,3H), 2.7(m,1H), 4.2(d,1H), 4.35(d,1H),
6.15(d,1H), 6.25(m,1H), 7.45(d,1H), 7.6(d,1H), 7.65(s,1H), 8.25(s,1H).
(i) 1.25(m,2H), 1.4(m,2H), 2.6(m,1H), 4.8(s,2H), 7.35(d,1H),
7.5(t,2H), 7.6(m,3H), 7.75(d,2H), 8.15(s,1H).
(j) 1.2(m,4H), 2.6(s,3H), 2.7(m,1H), 3.65(s,3H), 4.25(q,2H),
7.25(d1H), 7.3(d,1H), 8.15(s,1H).
(k) 1.2(m,2H), 1.3(m,2H), 2.5(s,3H), 2.65(m,1H, 3.9(d,1H),
3.95(d,1H), 7.3(dd,1H), 7.4(m,2H), 8.1(s,1H).
(l) 1.25(m,2H), 1.35(m,2H), 2.5(s,3H), 2.7(m,1H), 3.9(d,1H)
4.0(d,1H), 7.3(s,2H), 7.6(s,1H), 8.2(s,1H).
(m) 1.2(m,2H), 1.3(m,2H), 2.4(s,3H), 2.5(s,3H), 2.65(m,1H), 3.9
(d,1H), 3.95(d,1H), 7.1(d,1H), 7.25(s,1H), 7.4(d,1H), 8.15(d,1H).
(n) 1.15(m,4H), 2.35(s,3H), 2.58(m,1H), 4.8(q,2H), 7.35(dd,2H), 8.2(s,1H).

EXAMPLE 4

A mixture of 4-[3-chloro-4-methylsulphenyl-2-(methylsulphenylmethyl)benzoyl]-5-cyclopropylisoxazole (0.8 g), acetic anhydride (7 ml), acetic acid (25 ml) and hydrogen peroxide (30% w/v, 3.0 ml) was heated at 70° C. for 4 hours. After cooling, the solution was diluted (water), extracted (ethyl acetate), washed (water, then with ferrous sulphate solution, then with water), dried (magnesium sulphate) and evaporated to dryness, giving 4-[3-chloro-4-methylsulphonyl-2-(methylsulphonylmethyl)benzoyl]-5-cyclopropylisoxazole (compound 84, 0.63 g) as a white solid; m.p.89°–90° C. (forming a glass, m.p. 110° C.).

The following compounds were similarly prepared from appropriate starting materials: 5-cyclopropyl-4-[3,4-dichloro-2-(methylsulphonylmethyl)benzoyl]isoxazole (compound 85), m.p.142°–144° C.;

4-[4-chloro-2-methoxy-3-(methylsulphonylmethyl)benzoyl]-5-cyclopropylisoxazole (compound 86), m.p. 127°–127.5° C.;

5-cyclopropyl-4-[2,4-dichloro-3-(methylsulphonylmethyl)benzoyl]isoxazole (compound 87), m.p. 136°–138° C.

EXAMPLE 5

A crystal of iodine was added to a stirred suspension of magnesium (1.07 g) in methanol and the mixture heated under reflux conditions until a solution was obtained. 1-[4-Bromo-2-(methylsulphenylmethyl)phenyl]-3-cyclopropane-1,3-dione (13.09 g) was added whilst heating under reflux. After 1 hour the suspension was cooled, evaporated and re-evaporated after addition of toluene. The residue was dissolved in dichloromethane and a solution of ethyl chlorooximidoacetate (7.27 g) in dichloromethane was added to the stirred solution at 5° C. After 2 days, dilute hydrochloric acid was added and the organic phase was separated, washed (water), dried (magnesium sulphate) and evaporated. The residue was purified by chromatography eluting with ethyl acetate/hexane to give ethyl 4-[4-bromo-2-(methylsulphenylmethyl)benzoyl]-5-cyclopropylisoxazole-3-carboxylate (7.4 g), m.p. 42°–43° C.

By proceeding in a similar manner ethyl 4-[3-bromo-2-(methylsulphenylmethyl)benzoyl]-5-cyclopropylisoxazole-3-carboxylate, NMR (CDCl$_3$) 1.0–1.3 (m,4H), 1.1 (t,3H), 2.1 (s,3H), 2.0–2.2 (m,1H), 4.1 (m,4H), 7.1 (dd,1H), 7.3 (d,1H), 7.65 (d,1H).

REFERENCE EXAMPLE 1

A mixture of 2.2 g of 1-[4-bromo-2-(methylsulphenylmethyl)phenyl]-3-cyclopropylpropane-1,3-dione and 1.2 g of N,N-dimethylformamide dimethylacetal in toluene was heated at 80° C. for 6 hours. The mixture was then evaporated giving 1-[4-bromo-2-(methylsulphenylmethyl)phenyl]-3-cyclopropyl-2-N,N-dimethylaminomethylene-propane-1,3-dione as a viscous green oil (2.5 g), NMR (CDCl$_3$): 0.55 (2H,m), 0.85 (2H,m), 1.95 (4H,m), 2.70 (3H,s), 3.15 (3H,s), 3.88 (2H,s), 7.1–7.55 (4H,m).

Similarly prepared from the appropriate starting materials were compounds of formula (II) in which L represents NMe$_2$.

| R$^1$ | XR$^3$ | (R$^2$)$_n$ |
|---|---|---|
| cPr | 2-CH$_2$SMe | 4-Cl |
| cPr | 2-CH$_2$SEt | 4-Br |
| cPr | 2-CH$_2$SMe | 4-CF$_3$ (a) |
| cPr | 2-CH$_2$SMe | — |
| cPr | 2-CH$_2$SME | 4-SMe |
| cPr | 2-CH$_2$S-n-Pr | 4-Br |
| cPr | 2-CH$_2$S-i-Pr | 4-Br |
| cPr | 2-CH$_2$SEt | — |
| cPr | 2-CH$_2$SMe | 4-F |
| cPr | 2-CH$_2$SCH$_2$CH=CH$_2$ | 4-Br |
| cPr | 2-CH$_2$SMe | 3-F-4-OMe |
| cPr | 2-CH$_2$SCH$_2$CF$_3$ | 4-Br |
| cPr | 2-CH$_2$S-t-Bu | 4-Br |
| cPr | 2-CH$_2$S-Ph | 4-Br |
| cPr | 4-CH$_2$SMe | 2-Cl |
| cPr | 4-CH$_2$SMe | 2-F |
| cPr | 4-CH$_2$SMe | 2-Br |
| cPr | 4-CH$_2$SMe | 2-OMe |
| cPr | 4-CH$_2$SMe | 2-SMe |

(a) NMR(CDCl$_3$) 0.6(m,2H), 0.92(m,2H), 2.0(m,4H), 2.8(broad,3H),3.25(broad,3H), 3.95(s,2H), 7.5(m,3H), 7.61(s,1H).

REFERENCE EXAMPLE 2

A mixture of 1-[2-(methylsulphenyl)-3-(methylsulphenylmethyl)-4-chlorophenyl]-3-cyclopropylpropan-1,3-dione (1.5 g) and triethylorthoformate (8 ml) in acetic anhydride (25 ml) was heated at reflux temperature for 4 hours. The excess reagent and solvent were evaporated under reduced pressure, yielding 1-[2-(methylsulphenyl)-3-(methylsulphenylmethyl)-4-chlorophenyl]-2-ethoxymethylene-3-cyclopropylpropan-1,3-dione as a brown oil (2.3 g).

By proceeding in a similar manner 1-[4-chloro-3-(methylsulphenylmethyl)phenyl]-2-ethoxymethylene-3-cyclopropylpropan-1,3-dione was prepared.

Similarly prepared from appropriate starting materials were compounds of formula (II) in which L represents OEt.

| R$^1$ | XR$^3$ | (R$^2$)$_n$ |
|---|---|---|
| cPr | 2-CH$_2$SMe | 3-SMe-4Cl |
| cPr | 2-CH$_2$SMe | 3-CL-4SMe |
| cPr | 2-CH$_2$SMe | 3-F-4Cl |
| cPr | 3-CH$_2$SMe | 2-OMe-4Cl |
| cPr | 3-CH$_2$SMe | 2,4-Cl$_2$ |
| cPr | 2-CH$_2$SMe | 3,4-Cl$_2$ |
| cPr | 2-CH$_2$SMe | 3-Br-4Cl |
| cPr | 3-CH$_2$SMe | 2-Cl-4SMe |
| cPr | 2-CH$_2$SMe | 3-Br |
| cPr | 2-CH$_2$SEt | 3,4-Cl$_2$ |
| cPr | 2-CH$_2$(Me)SMe | 3,4-Cl$_2$ |
| cPr | 3-CH$_2$SEt | 2-SMe-4Cl |

REFERENCE EXAMPLE 3

A solution of cyclopropyl methyl ketone (1.1 g) and methyl 4-bromo-2-(methylsulphenylmethyl)benzoate (3.6 g) in tetrahydrofuran was added to a refluxing suspension of sodium hydride (80%, 0.9 g) in tetrahydrofuran. After the addition was complete, the mixture was maintained at reflux temperature for 30 minutes. It was then cooled and poured onto 100 g of ice and 50 ml of saturated aqueous sodium bicarbonate. The mixture was extracted with hexane, the organic solution dried (anhydrous sodium sulphate) and the solvent evaporated to give 1-[4-bromo-2-(methylsulphenylmethyl)phenyl]-3-cyclopropylpropan-1,3-dione as an orange oil (2.23 g), NMR (CDCl$_3$): 1.00 (2H,m), 1.20 (2H,m), 1.75 (1H,m), 2.03 (3H,s), 3.92 (2H,s), 6.00 (1H,s), 7.35 (1H,m), 7.45 (1H,m), 7.58 (1H,m) 14.74 (1H,s).

By proceeding in a similar manner the following compounds were prepared:

1-[4-chloro-2-(methylsulphenyl)-3-methylsulphenylmethyl)phenyl]-3-cyclopropylpropan-1,3-dione, NMR (CDCl$_3$): 0.95 (2H,m), 1.20 (2H,m), 1.75 (1H,m), 2.2 (3H,s), 2.45 (3H,s), 4.25 (2H,s), 6.05 (1H,s), 7.3 (2H,q), 15.8 (1H,s);

1-[4-chloro-3-(methylsulphenylmethyl)phenyl]-3-cyclopropylpropan-1,3-dione, NMR (CDCl$_3$) 0.9 (2H,m), 1.1 (2H,m), 1.7 (1H, m) 1.9 (3H,s), 3.7 (2H,s) 6.1 (1H,s), 7.3 (1H,d), 7.55 (1H,m), 7.7 (1H,d), 16.1 (1H,s).

Similarly prepared were the following compounds of formula (VI).

| R$^1$ | XR$^3$ | (R$^{21}$)$_n$ | m.p.(°C.)/ NMR |
|---|---|---|---|
| cPr | 2-CH$_2$SMe | 4-Cl | (a) |
| cPr | 2-CH$_2$SEt | 4-Br | (b) |
| cPr | 2-CH$_2$SMe | 4-CF$_3$ | 57–58 |
| cPr | 2-CH$_2$SMe | 4-SMe | (c) |
| cPr | 2-CH$_2$S-n-Pr | 4-Br | (d) |
| cPr | 2-CH$_2$S-i-Pr | 4-Br | (e) |
| cPr | 2-CH$_2$SCH$_2$CH=CH$_2$ | 4-Br | (f) (2) |
| cPr | 2-CH$_2$SCH$_2$CF$_3$ | 4-Br | (g) |
| cPr | 2-CH$_2$S-t-Bu | 4-Br | (h) |
| cPr | 2-CH$_2$S-Ph | 4-Br | (i) |

-continued

| | | | |
|---|---|---|---|
| cPr | 4-CH$_2$SMe | 2-Cl | (j) |
| cPr | 4-CH$_2$SMe | 2-F | (k) |
| cPr | 4-CH$_2$SMe | 2-Br | (k) |
| cPr | 4-CH$_2$SMe | 2-OMe | (l) (1) |
| cPr | 4-CH$_2$SMe | 2-SMe | (m) |
| cPr | 2-CH$_2$SMe | 3-SMe-4-Cl | (n) |
| cPr | 2-CH$_2$SMe | 3-Cl-4SMe | 89–90 |
| cPr | 2-CH$_2$SMe | 3-F-4Cl | (o) |
| cPr | 3-CH$_2$SMe | 2-OMe-4-Cl | (p) |
| cPr | 3-CH$_2$SMe | 2,4-Cl$_2$ | 74–75 |
| cPr | 2-CH$_2$SMe | 3,4-Cl$_2$ | (q) |
| cPr | 2-CH$_2$SMe | 3-Br-4-Cl | (r) |
| cPr | 3-CH$_2$SMe | 2-Cl-4SMe | (s) |
| cPr | 2-CH$_2$SMe | 3-Br | 61–65 |
| cPr | 2-CH$_2$SMe | 3,4-Cl$_2$ | (t) |
| cPr | 2-CH$_2$(Me)SMe | 3,4-Cl$_2$ | (u) |
| cPr | 2-CH$_2$SMe | — | (v) |
| cPr | 2-CH$_2$SEt | — | (w) |
| cPr | 2-CH$_2$SMe | 4-F | (x) |
| cPr | 2-CH$_2$SMe | 3-F-4-OMe | (y) |

(1) Obtained as a by-product during the reaction of methyl 2-fluoro-4-methylsulphenylmethylbenzoate with cyclopropyl methyl ketone.
(2) Obtained as a mixture with the corresponding double bond isomer 1-{4-bromo-2-[(1-propenyl)sulphenylmethyl]phenyl}-3-cyclopropyl-1,3-dione.

NMR (in CDCl$_3$ unless otherwise stated):
(a) 0.85(m,2H), 1.05(m,2H), 1.6(m,1H), 1.9(s,3H), 3.8(s,2H), 5.4(s,1H), 7.1(d,1H), 7.25(s,1H), 7.30(d,1H), 15.95(s,1H).
(b) 0.75(m,2H), 0.95(m,2H), 1.65(m,1H), 2.1(t,3H), 2.4(q,2H), 3.85(s,2H), 5.95(s,1H), 7.2(d,1H), 7.3(d,1H), 7.5(s,1H), 16.0(s,1H).
(c) 1.0(m,2H), 1.25(m,2H), 1.8(m,1H), 2.1(s,3H), 2.55(s,3H),4.0(s,2H), 6.05(s,1H), 7.1(d,1H), 7.25(s,1H), 7.4(d,1H), 16.25(s,1H).
(d) 1.0(t,3H), 1.05(m,2H, 1.25(m,2H), 1.6(m,2H),1.75(m,1H), 2.45(t,2H), 3.95(s,2H), 6.05(s,1H), 7.35(d,1H), 7.4(d,1H), 7.6(s,1H), 16.1(s,1H).
(e) 1.0(m,2H), 1.2(m,2H), 1.3(d,6H), 1.8(m,1H), 2.9(m,1H), 3.95(s,2H), 6.05(s,1H), 7.3(d,1H), 7.4(d,1H), 7.6(s,1H), 16.25(s,1H).
(f) 1.0(m,2H), 1.2(m,2H), 1.75(m,1H), 3.1(d,2H), 3.9(s,2H), 5.1(dd,2H), 5.75(m,1H), 6.05(s,1H), 7.35(d,1H), 7.45(d,1H), 7.55(s,1H), 16.1(s,1H).
(g) 0.9(m,2H), 1.15(m,2H), 1.75(m,1H), 2.95(m,2H), 3.85(s,2H), 5.95(s,1H), 7.4(d,1H), 7.45(s,1H), 7.75(d,1H), 16.1(s,1H).
(h) 0.9(m,2H), 1.1(m,2H), 1.25(s,9H), 1.65(m,1H), 3.85(s,2H), 6.0(s,1H), 7.2(d,1H), 7.3(d,1H), 7.5(s,1H), 16.0(s,1H).
(i) 0.7(m,2H), 0.9(m,2H), 1.6(m,1H), 4.25(s,2H), 5.8(s,1H), 7.1(m,5H), 7.3(d,1H), 7.35(d,1H), 7.3(s,1H), 15.95(s,1H).
(j) 1.0(m,2H), 1.2(m,2H), 1.75(m,1H), 2.0(s,3H), 3.6(s,2H), 6.2(s,1H), 7.2(dd,1H), 7.4(d,1H), 7.6(d,1H), 1.59(bs,1H).
(k) 1.0(m,2H), 1.2(m,2H), 1.75(m,1H), 2.0(s,3H), 3.6(s,2H), 6.1(s,1H), 7.25(dd,1H), 7.5(d,1H), 7.6(d,1H), 16.0(bs,1H).
(l) 1.9(s,3H), 3.6(s,2H), 3.85(s,3H), 7.05(m,2H), 7.85(t,1H).
(m) 1.0(m,2H), 1.3(m,2H), 1.75(m,1H), 2.0(bs,3H), 2.5(s,3H), 3.7(bs,2H), 6.1(s,1H), 7.1(d,1H), 7.2(s,1H), 7.5(d,1H), 16.1(bs,1H).
(n) 0.9(m,2H), 1.15(m,2H), 2.0(s,3H), 2.3(s,3H), 4.28(s,2H), 5.9(s,1H), 7.25(dd,2H), 15.9(s,1H).
(o) 1.1(m,4H), 1.7(m,1H), 2.05(d,3H), 3.95(d,2H), 6.0(s,1H), 7.2(m,2H), 16.0(s,1H).
(p) 0.9(m,2H), 1.15(m,2H), 1.75(m,1H), 2.1(s,3H), 3.8(s,3H), 3.9(s,2H), 6.4(s,1H), 7.25(d,1H), 7.6(d,1H), 16.15(s,1H).
(q) 1.1(m,4H), 1.7(m,1H), 2.1(s,3H), 4.1(s,2H), 6.0(s,1H), 7.25(dd,2H), 15.9(s,1H).
(r) 1.05(m,2H), 1.22(m,2H), 1.75(m,1H), 2.1(s,3H), 4.2(s,2H), 6.0(s,1H), 7.35(d,1H), 7.4(d,1H), 16.0(bs,1H).
(s) 1.0(m,4H), 1.7(m,1H), 2.1(s,3H), 2.5(s,3H), 4.0(s,2H), 6.0(s,1H), 7.25(dd,2H), 16.0(s,1H).
(t) 0.95(m,4H), 1.25(t,3H), 1.75(m,1H), 2.6(q,2H), 4.2(s,2H), 6.05(s,1H), 7.3(d,1H), 7.4(d,1H), 16.0(bs,1H).
(u) 1.0(m,4H), 1.7(d,3H), 1.8(m,1H), 1.95(s,3H), 3.7(m,2H), 7.0(d,1H), 7.35(d,1H).
(v) 0.95(m,2H), 1.13(m,2H), 1.71(m,1H), 1.92(s,3H), 4.08(s,2H), 5.98(s,1H), 7.32(m,4H), 16.06(s,1H).,
(w) 0.95(m,2H), 1.15(m,5H), 1.69(m,1H), 2.4(q,2H), 3.93(s,2H), 6.0(s,1H), 7.32(m,4H), 16.05(broad,1H).
(x) 0.93(m,2H), 1.12(m,2H), 1.68(m,1H), 1.98(s,3H), 3.88(s,2H), 5.93(s,1H), 6.90(m,1H), 7.07(dd,1H), 7.45(m,1H).
(y) 1.0(m,2H), 1.2(m,2H), 1.73(m,1H), 2.1(s,3H), 3.92(s,3H), 4.07(s,2H), 6.08(s,1H), 6.88(dd,1H), 7.32(d,1H), 16.22(broad,1H).

REFERENCE EXAMPLE 4

A mixture of methyl 4-bromo-2-(bromomethyl)benzoate (12 g) and sodium thiomethoxide (2.5 g) in toluene was stirred at 100° C. for 2 hours. The mixture was then cooled, poured into water and extracted with ethyl acetate. The organic layer was separated, washed with brine, dried (anhydrous sodium sulphate) and evaporated to afford a brown oil which was purified by column chromatography on silica gel giving methyl 4-bromo-2-(methylsulphenylmethyl)benzoate (4.1 g) as white crystals, m.p. 79.3° C.

By proceeding in a similar manner the following compounds of formula (XII) above were prepared:

| R$^{11}$ | R$^1$ | XR$^3$ | (R$^2$)$_n$ | b.p.(°C.)/NMR |
|---|---|---|---|---|
| Me | cPr | 2-CH$_2$SMe | 3,4-Cl$_2$ | (a) |
| Et | cPr | 2-CH$_2$SMe | 3-F-4-Cl | (d) |
| Me | cPr | 2-CH$_2$SMe | 2-F-4-Cl | (b) |
| Et | cPr | 2-CH$_2$SMe | 2,4-Cl$_2$ | (e) |
| Et | cPr | 2-CH$_2$SMe | 3-Br-4-Cl | (f) |
| Et | cPr | 2-CH$_2$SMe | 3-Br | (g) |
| Et | cPr | 2-CH$_2$SEt | 3,4-Cl$_2$ | (h) |
| Me | cPr | 2-CH$_2$(Me)SMe | 3,4-Cl$_2$ | (c) |
| Me | cPr | 4-CH$_2$SMe | 2-Br | (i) |
| Me | cPr | 4-CH$_2$SMe | 2-Cl | (j) |
| Me | cPr | 4-CH$_2$SMe | 2-F | (k) |
| Me | cPr | 2-CH$_2$SMe | 4-CF$_3$ | (l) |
| Me | cPr | 2-CH$_2$SMe | — | (m) |
| Me | cPr | 2-CH$_2$SEt | — | (n) |
| Me | cPr | 2-CH$_2$SMe | 3,4-F$_2$ | (o) |
| Me | cPr | 2-CH$_2$SMe | 4-F | (p) |
| Me | cPr | 2-CH$_2$SEt | 4-Br | (q) |
| Me | cPr | 2-CH$_2$S-n-Pr | 4-Br | (1) |
| Me | cPr | 2-CH$_2$S-i-Pr | 4-Br | (2) |
| Me | cPr | 2-CH$_2$SCH$_2$CF$_3$ | 4-Br | (r) |
| Me | cPr | 2-CH$_2$SMe | 4-Cl | 41–44 |
| Me | cPr | 3-CH$_2$SEt | 2-F-4Cl | |

It is to be understood that alternative inert solvents (e.g. tetrahydrofuran, or N,N-dimethylformamide) may be used in this reaction, and that the sodium salt of the thiol may be generated in situ by employing a base (preferably potassium carbonate, sodium carbonate or sodium hydride). A suitable catalyst (e.g. sodium iodide or tetraethyl ammonium iodide) may optionally be present in the reaction mixture.

Note
(1) b.p. 136–140° C. (0.7 torr)
(2) b.p. 130–137° C. (0.7 torr)

NMR (in CDCl$_3$ unless otherwise stated):
(a) 2.0(s,3H), 3.8(s,3H), 4.3(s,2H), 7.35(d,1H), 7.65(d,1H).
(b) 2.1(d,3H), 3.85(d,2H), 3.9(s,3H), 7.21(dd,1H), 7.8(t,1H).
(c) 1.65(d,3H), 1.9(s,3H), 3.85(s,3H), 4.65(q,1H), 7.32(m,2H).
(d) 1.4(t,3H), 2.0(s,3H), 4.1(d,2H), 4.35(q,2H), 7.45(m,2H).
(e) 1.4(t,3H), 2.15(s,3H), 4.1(s,2H), 4.35(q,2H), 7.4(dd,2H).
(f) 1.25(t,3H), 2.0(s,3H), 4.25(q,2H), 4.3(s,2H), 7.5(m,2H).
(g) 1.45(t,3H), 2.0(s,3H), 4.3(q,2H), 7.1(dd,2H), 7.6(d,1H), 7.7(d,1H).
(h) 1.2(t,3H), 1.35(t,3H), 2.5(q,2H), 4.35(q,2H), 4.35(s,2H), 7.55(m,2H).
(i) 1.9(s,3H), 3.6(s,2H), 3.85(s,3H), 7.25(dd,1H), 7.55(d,1H), 7.7(d,1H).
(j) 1.9(s,3H), 3.6(s,2H), 3.9(s,3H), 7.2(dd,1H), 7.35(d,1H), 7.7(d,1H).
(k) 1.9(s,3H), 3.6(s,2H), 3.85(s,3H), 7.05(m,2H), 7.85(t,1H).
(l) 1.93(s,3H), 3.86(s,3H), 4.04(s,2H), 7.5(m,2H), 7.96(m,1H).
(m) 1.92(s,3H), 3.8(s,3H), 4.04(s,2H), 7.25(m,2H), 7.37(dd,1H), 7.84(dd,1H).
(n) 1.21(t,3H), 2.45(q,2H), 3.1(s,3H), 4.12(s,2H), 7.28(m,2H), 7.4(m,1H), 7.9(d,1H).
(o) 2.06(s,3H), 3.91(s,3H), 4.18(s,2H), 7.12(dd,1H), 7.77(m,1H).
(p) 1.9(s,3H), 3.77(s,3H), 39.5(s,2H), 6.86(m,1H), 7.83(dd,1H), 7.93(dd,1H).
(q) 1.25(t,3H), 2.45(q,2H), 3.9(s,3H), 4.1(s,2H), 7.45(d,1H), 7.55(s,1H), 7.8(d,1H).
(r) 3.05(q,2H), 3.9(s,3H), 4.7(s,2H), 7.45(s,1H), 7.5(d,1H), 7.85(d,1H).

REFERENCE EXAMPLE 5

A mixture of methyl 4-chloro-2-fluoro-3-(bromomethyl)benzoate (8.6 g) and sodium thiomethoxide (2.1 g) in tetrahydrofuran was stirred at 50° C. for 5 hours and allowed to cool to room temperature. The reaction mixture was quenched with water, followed by extraction with diethyl ether, drying of the organic phase (anhydrous sodium sulphate) and evaporation of the solvent to yield methyl 4-chloro-2-(methylsulphenyl)-3-(methylsulphenylmethyl)benzoate (7.4 g), NMR (CDCl$_3$): 2.1 (3H,s), 2.35 (3H,s), 3.85 (3H,s), 4.2 (2H,s) 7.3 (2H,m).

By proceeding in a similar manner methyl 4-chloro-3-(methylsulphenylmethyl)benzoate was prepared as a white solid, m.p. 47.1° C.

The following compounds were also similarly prepared from appropriate starting materials:
  Methyl 4-methylsulphenyl-2-(methylsulphenylmethyl)benzoate from methyl 4-bromo-2-(bromomethyl)benzoate using N,N-dimethylformamide as solvent.
  Methyl 3-chloro-4-methylsulphenyl-2-(methylsulphenylmethyl)benzoate from methyl 3,4-dichloro-2-(methylsulphenylmethyl)benzoate, using methanethiol and potassium carbonate in N,N-dimethylformamide as solvent.
  Methyl 2-methylsulphenyl-4 -(methylsulphenylmethyl)benzoate.

REFERENCE EXAMPLE 6

A mixture of methyl 2-fluoro-4-methylsulphenylbenzoate (4.1 g), sodium thiomethoxide (1.48 g) and N,N-dimethylformamide (16 ml) was stirred at 50° C. for 18 hours, poured onto water and extracted (ethyl acetate). The extract was washed (water), dried (magnesium sulphate) and evaporated to give methyl 2-methylsulphenyl-4-methylsulphenylbenzoate (2.09 g) as an orange oil, NMR (CDCl$_3$) 2.0 (s,3H), 2.4 (s,3H), 3.65 (s,2H), 3.9 (s,3H), 7.05 (dd,1H), 7.15 (d,1H), 7.9 (d,1H).

Similarly prepared from ethyl 2,4-dichloro-3-methylsulphenylbenzoate was ethyl 2-chloro-4-methylsulphenyl-3-methylsulphenylmethylbenzoate NMR (CDCl$_3$) 1.4 (t,3H), 2.15 (s,3H), 2.5 (s,3H), 4.05 (s,2H), 7.1 (d,1H), 7.65 (d,1H); and from methyl 4-chloro-3-ethylsulphenylmethyl-2-fluorobenzoate was prepared methyl 4-chloro-3-ethylsulphenylmethyl-2-methylsulphenylbenzoate, NMR (CDCl$_3$) 1.1 (t,3H), 2.4 (s,3H), 2.6 (d,2H), 3.9 (s,3H), 4.2 (s,2H), 7.3 (2dd,2H).

REFERENCE EXAMPLE 7

Separate solutions of ethyl 3-amino-4-chloro-2-methylsulphenylbenzoate (53.0 g) in chloroform, and t-butyl nitrite (36 ml) were added during 0.5 hours to stirred dimethyl disulphide (38.1 ml) at such a rate that the exotherm was controlled. After a further 2 hours water was added and the organic layer washed with dilute hydrochloric acid, dried (magnesium sulphate) and evaporated. The residue was purified by chromatography eluting with ethyl acetate/petroleum ether to give ethyl 4-chloro-3-methylsulphenyl-2-methylsulphenylmethylbenzoate (22.3 g) as a yellow oil, NMR (CDCl$_3$) 1.35 (t,3H), 2.1 (s,3H), 2.4 (s,3H), 4.35 (q,2H), 4.6 (s,2H), 7.55 (dd,2H).

REFERENCE EXAMPLE 8

N-chlorosuccinimide (215 g) was added during 10 minutes to a solution containing ethyl 3-amino-4-chlorobenzoate (108 g) and dimethyl sulphide (117 ml) in dichloromethane maintaining below 0° C. Triethylamine (80 ml) was added and after 20 minutes further additions of dimethyl sulphide (117 ml), N-chlorosuccinimide (215 g) and triethylamine (80 ml) were made. After 0.5 hours additional triethylamine (280 ml) was introduced, the mixture heated under reflux conditions overnight and evaporated. Ether was added and this was washed with water, dilute sodium bicarbonate, dried (magnesium sulphate) and evaporated. Purification by chromatography, eluting with ethyl acetate/petroleum ether gave ethyl 3-amino-4-chloro-2-methylsulphenylmethylbenzoate (47.6 g), NMR (CDCl$_3$) 1.45 (t,3H), 2.1 (s,3H), 4.1 (s,2H), 4.3 (q,2H), 4.7 (s,2H), 7.2 (m,2H).

REFERENCE EXAMPLE 9

A solution of methyl 4-chloro-2-fluoro-3-methylsulphenylmethylbenzoate (11.4 g) in tetrahydrofuran was stirred, with addition of sodium methoxide (3.5 g). After 2 hours water was added and the mixture extracted with ether, dried (magnesium sulphate) and evaporated to give methyl 4-chloro-2-methoxy-3-methylsulphenylmethylbenzoate (10.1 g), NMR (CDCl$_3$) 2.15 (s,3H), 3.9 (3s,8H), 7.15 (d,1H), 7.65 (d,1H).

REFERENCE EXAMPLE 10

Methyl 4-bromo-2-bromomethylbenzoate (24.6 g) was added to a stirred mixture of allylmercaptan (70%, 9 g), sodium ethoxide (5.77 g) and tetrabutylammonium iodide (0.4 g) for 15 minutes. Cold sodium bicarbonate solution was added and the mixture extracted with ether. The extract was washed with brine, dried (magnesium sulphate) and evaporated to give methyl 4-bromo-2-(2-propenylsulphenylmethyl)benzoate (2.41 g), NMR (CDCl$_3$) 3.05 (d,2H), 3.9 (s,3H), 4.0 (s,2H), 5.1 (m,2H), 5.75 (m,1H), 7.4 (d,1H), 7.5 (s,1H), 7.75 (d,1H).

Similarly prepared were the following compounds:
  Methyl 4-bromo-2-phenylsulphenylmethylbenzoate, NMR (CDCl$_3$) 3.9 (s,3H), 4.5 (s,2H), 7.3 (m,5H), 7.35 (s,1H), 7.45 (d,1H), 7.8 (d,1H).
  Methyl 4-bromo-2-tert-butylsulphenylmethylbenzoate. NMR (CDCl$_3$) 1.4 (s,9H), 3.9 (s,3H), 4.15 (s,2H), 7.4 (d,1H), 7.65 (s,1H), 7.75 (d,1H).

REFERENCE EXAMPLE 11

Carbon tetrachloride (0.1 ml) was added to magnesium turnings (0.3 g) in dry methanol and when the magnesium had dissolved, t-butyl 3-cyclopropyl-3-oxopropionate (2.0 g) was added at 30° C. The mixture was heated and stirred at 60° C. for 0.5 hours, dissolved in toluene and evaporated to give t-butyl 3-cyclopropyl-3-oxopropionate magnesium enolate (2.5 g) as a solid. This was stirred in toluene and a solution of 4-chloro-3-ethylsulphenylmethyl-2-methylsulphenylbenzoyl chloride (3.3 g) in toluene added. After 12 hours, the solution was washed with dilute hydrochloric acid and with water and evaporated to give t-butyl 2-[4-chloro-3-ethylsulphenylmethyl-2-(methylsulphenyl)benzoyl]-3-cyclopropyl-3-oxopropionate (4.6 g) as a brown oil. This was dissolved in dry toluene and stirred with addition of p-toluenesulphonate (0.13 g). The mixture was stirred and heated at reflux for 6 hours, cooled, washed with water, dried (magnesium sulphate) and evaporated to give 1-[4-chloro-3-ethylsulphenylmethyl-2-(methylsulphenyl)phenyl]-3-cyclopropan-1,3-dione (2.3 g) as a brown oil, NMR (CDCl$_3$) 1.0 (m,2H), 1.2 (m,2H), 1.3

(m,1H), 2.4 (s,3H), 2.7 (q,2H), 4.3 (s,2H), 6.1 (s,1H), 7.3 (d,1H), 7.4 (d,1H), 15.9 (s,1H).

REFERENCE EXAMPLE 12

Methanol (2 drops) was added to a mixture of sodium hydride (0.9 g) and tetrahydrofuran heated under reflux conditions. A mixture of methyl 4-chloro-3-ethylsulphenylmethyl-2-methylsulphenylbenzoate (4.0 g) and methyl cyclopropyl ketone (2.5 g) in tetrahydrofuran (36 ml) was added during 0.5 hours whilst maintaining at reflux. The mixture was stirred overnight at ambient temperature, and then quenched with methanol. Ether and water were added and the aqueous layer acidified (dilute hydrochloric acid), extracted (ether) and the ethereal solution extracted (sodium carbonate solution). This basic extract was re-acidified (hydrochloric acid), extracted (ether) and evaporated to give 4-chloro-3-ethylsulphenylmethyl-2-methylsulphenylbenzoic acid (3.0 g), NMR (CDCl$_3$) 1.35 (t,3H), 2.5 (s,3H), 2.7 (q,2H), 4.3 (s,2H), 7.5 (d,1H), 7.8 (d,1H).

REFERENCE EXAMPLE 13

A mixture of ethyl 3,4-dichloro-2-methylbenzoate (34.0 g), N-bromosuccinimide (30.0 g) and carbon tetrachloride was irradiated with u.v. light in a photochemical reactor for 3 hours. The cooled mixture was filtered and the filtrate washed with water, dried (magnesium sulphate) and evaporated to give ethyl 2-bromomethyl-3,4-dichlorobenzoate (51.0 g) as an oil, NMR (CDCl$_3$) 1.45 (t,3H), 4.4 (q,2H), 5.15 (s,2H), 7.7 (m,2H).

By proceeding in a similar manner the following alkyl α-bromoalkyl benzoates of formula (XII) above were prepared from the appropriate toluenes. In some cases the u.v. light was replaced by a tungsten lamp, in which case a radical initiator (azobis-isobutyronitrile) was also added to the reaction mixture.

| $R^{11}$ | X-$R^3$ | $(R^{21})_n$ | m.p.(°C.) /NMR |
|---|---|---|---|
| Et | 2-CH$_2$Br | 3-F-4-Cl | (a) |
| Me | 3-CH$_2$Br | 2-F-4-Cl | (b) |
| Et | 3-CH$_2$Br | 2,4-Cl$_2$ | (c) |
| Et | 2-CH$_2$Br | 3-Br-4-Cl | (d) |
| Et | 2-CH$_2$Br | 3-Br | (e) |
| Me | 2-CH(Me)Br | 3,4-Cl$_2$ | (f) |
| Me | 4-CH$_2$Br | 2-Br | — |
| Me | 4-CH$_2$Br | 2-Cl | (g) |
| Me | 4-CH$_2$Br | 2-F | (h) |
| Me | 2-CH$_2$Br | 4-CF$_3$ | (i) |
| Me | 2-CH$_2$Br | 3,4-F$_2$ | (j) |
| Me | 2-CH$_2$Br | 4-F | (k) |

NMR (CDCl$_3$ unless otherwise stated).
(a) 1.4(t,3H), 4.4(q,2H), 5.0(d,2H), 7.6(m,2H).
(b) 3.9(s,3H), 4.6(d,2H), 7.2(dd,1H), 7.8(t,1H).
(c) 1.3(t,3H), 4.4(q,2H), 4.8(s,2H), 7.5(dd,2H).
(d) 1.35(t,3H), 4.35(q,2H), 5.15(s,2H), 7.6(m,2H).
(e) 1.4(t,3H), 4.35(q,2H), 7.15(dd,1H), 7.7(d,1H), 7.8(d,1H).
(f) 2.1(d,3H), 3.9(s,3H), 6.0(q,1H), 7.4(m,2H).
(g) 3.9(s,3H), 4.45(s,2H), 7.3(dd,1H), 7.5(d,1H), 7.8(d,1H).
(h) 3.95(s,3H), 4.4(s,2H), 7.2(m,2H), 7.9(t,1H).
(i) 3.92(s,3H), 4.9(s,2H), 7.95(d,1H), 7.68(s,1H), 8.0(d,1H).
(j) 3.97(s,3H), 5.0(s,2H), 7.2(dd,1H), 7.84(m,1H).
(k) 3.94(s,3H), 4.94(s,2H), 7.07(m,1H), 7.2(dd,1H), 8.02(m,1H)

REFERENCE EXAMPLE 14 n-Butyl lithium (2.5M in hexanes, 180 ml) was added during 1 hour to a stirred solution of 3,4-dichlorobenzoic acid (40.0 g) at −78° C. and stirring maintained at that temperature overnight. A solution of methyl iodide (72 ml) in tetrahydrofuran was then added during 1.5 hours and the mixture kept at −78° C. for 3 hours and allowed to warm to room temperature overnight. The solvent was evaporated and the mixture added to water, acidified (concentrated hydrochloric acid) and extracted (ethyl acetate). The extract was dried (magnesium sulphate), evaporated and triturated (ether) to give 3,4-dichloro-2-methylbenzoic acid (33.3 g) as a white solid, m.p. 177°–178° C.

The following compounds were prepared in a similar manner:

4-chloro-3-fluoro-2-methylbenzoic acid, m.p. 174.5°–175° C.;
4-chloro-2-fluoro-3-methylbenzoic acid, NMR (CDCl$_3$) 2.1 (s,3H), 7.0 (dd,1H), 7.5 (t,1H), from 2-chloro-6-fluorotoluene;
3,4-dichloro-2-ethylbenzoic acid, m.p. 120°–123° C.;
3,4-difluoro-2-methylbenzoic acid, m.p. 152.5°–153.5° C.

REFERENCE EXAMPLE 15 n-Butyl lithium (2.5M in hexanes, 176 ml) was added to a stirred solution of 1-bromo-4-chloro-3-fluorobenzene (83.38 g) in dry ether. Stirring was maintained for a further 2.5 hours at −78° C., and the mixture poured onto excess solid carbon dioxide pellets, allowed to reach room temperature and water added. The mixture was washed with ether, acidified, extracted (ethyl acetate) and dried (magnesium sulphate). After evaporation the residue was triturated with petroleum ether to give 4-chloro-3-fluorobenzoic acid (66.4 g) as a white solid, m.p. 192°–192.5° C.

REFERENCE EXAMPLE 16

Bromine (48 ml) was added to a stirred solution of sodium hydroxide (120 g) in water. (2,4-Dichloro-3-methyl)acetophenone (33.9 g) was added at 60° C., and stirring continued at this temperature for 3 hours. The mixture was cooled, washed (ethyl acetate) and the aqueous layer acidified (concentrated hydrochloric acid) and extracted (ethyl acetate). The extract was dried (magnesium sulphate) and evaporated to give 2,4-dichloro-3-methylbenzoic acid (32.9 g) as a cream solid, NMR (CDCl$_3$) 2.55 (s,3H), 7.6 (dd,2H).

REFERENCE EXAMPLE 17

Aluminium chloride (144 g) was added to a stirred mixture of 2,6-dichlorotoluene (43 g) and acetyl chloride (86 g) in dichloromethane and the mixture then heated under reflux conditions for 26 hours. After standing at ambient temperature for 3 days the mixture was poured onto ice/hydrochloric acid and the organic layer washed in turn with dilute hydrochloric acid, water, sodium hydroxide solution and water. The dried (over magnesium sulphate) solution was evaporated and the residue recrystallised from petroleum ether to give (2,4-dichloro-3-methyl)acetophenone (33.8 g), NMR (CDCl$_3$) 2.5 (s,3H), 2.6 (s,3H), 7.35 (dd,2H).

REFERENCE EXAMPLE 18

A solution of sodium nitrite (13 g) in concentrated sulphuric acid was added during 0.5 hours to a solution of ethyl 3-amino-4-chloro-2-methylbenzoate (22.4 g) in acetic acid, keeping the temperature below 15° C. After stirring for a further 1 hour at 5° C., the resulting diazonium mixture was added during 0.75 hours to a solution of copper (I) bromide (31 g) in hydrobromic acid (45%, 103 ml) and water. Heating to 40° C. was continued for a further 2 hours before addition of water and extraction (ethyl acetate). The extract was washed (sodium hydroxide solution), dried (magnesium sulphate) and evaporated to give ethyl 3-bromo-4-chloro-2-methylbenzoate (22.2 g) as a brown oil, NMR (CDCl$_3$) 1.3 (t,3H), 2.65 (s,3H), 4.3 (q,2H), 7.45 (m,2H).

Similarly prepared was ethyl 3-bromo-2-methylbenzoate, NMR (CDCl$_3$) 1.6 (t,3H), 2.6 (s,3H), 4.4 (q,2H), 7.1 (dd,1H), 7.65 (d, 1H), 7.7 (d,1H).

REFERENCE EXAMPLE 19

A solution of ethyl 3-amino-4-chloro-2-(methylsulphenylmethyl)benzoate (50 g) in ethanol was added to a stirred suspension of Raney Nickel (300 g) in ethanol. After stirring overnight at room temperature, a further addition of Raney Nickel was made and the mixture stirred for 2 hours. Water was added, the mixture filtered and the residue washed with dichloromethane. The filtrate was evaporated, re-extracted with ethyl acetate, dried (magnesium sulphate) and evaporated to give ethyl 3-amino-4-chloro-2-methylbenzoate (29.7 g) as a brown oil, NMR (CDCl$_3$) 1.25 (t,3H), 2.25 (s,3H), 4.3 (q,2H), 7.05 (m,2H).

Acid chlorides in which a group —XR$^3$ was not in the position ortho to the carboxyl group were prepared by reaction of the corresponding benzoic acid with thionyl chloride at the reflux temperature of the mixture.

Ethyl benzoates were prepared by reaction of the corresponding benzoic acids by reaction with the corresponding alcohol and heating under reflux conditions in the presence of a strong acid (concentrated sulphuric acid).

According to a feature of the present invention, there is provided a method for controlling the growth of weeds (i.e. undesired vegetation) at a locus which comprises applying to the locus a herbicidally effective amount of at least one 4-benzoylisoxazole derivative of formula (I). For this purpose, the 4-benzoylisoxazole derivatives are normally used in the form of herbicidal compositions (i.e. in association with compatible diluents or carriers and/or surface active agents suitable for use in herbicidal compositions), for example as hereinafter described. The compounds of formula (I) show herbicidal activity against dicotyledonous (i.e. broad-leafed) and monocotyledonous (i.e. grass) weeds by pre- and/or post-emergence application. By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of formula (I) may be used to control the growth of:

broad-leafed weeds, for example, *Abutilon theophrasti, Amaranthus retroflexus, Bidens pilosa, Chenopodium album, Galium aparine, Ipomoea spp.* e.g. *Ipomoea purpurea, Sesbania exaltata, Sinapis arvensis, Solanum nigrum* and *Xanthium strumarium,* and grass weeds, for example *Alopecurus myosuroides, Avena fatua, Digitaria sanguinalis, Echinochloa crusgalli, Sorghum bicolor, Eleusine indica* and *Setaria spp.* e.g. *Setaria faberii* or *Setaria viridis,* and sedges, for example, *Cyperus esculentus.*

The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates between 0.01 kg and 5 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates between 0.01 kg and 4.0 kg, and preferably between 0.01 kg and 2.0 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates between 0.25 kg and 5.0 kg, and preferably between 0.5 kg and 4.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates between 1.0 kg and 20.0 kg, and preferably between 5.0 and 10.0 kg, of active material per hectare are particularly suitable for this purpose.

When used to control the growth of weeds by pre-emergence application, the compounds of formula (I)

may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact the soil and may also then exercise a pre-emergence control on later-germinating weeds in the soil.

Where especially prolonged weed control is required, the application of the compounds of formula (I) may be repeated if required.

According to a further feature of the present invention, there are provided compositions suitable for herbicidal use comprising one or more of the 4-benzoylisoxazole derivatives of formula (I), in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent. Surface-active agents which may be present in herbicidal compositions of the present invention may be of the ionic or nonionic types, for example sulphoricinoleates, quaternary ammonium derivatives, products based on condensates of ethylene oxide with alkyl and polyaryl phenols, e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

When desired, liquid compositions of the compound of formula (I) may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Unless otherwise specified, the following percentages are by weight. Preferred herbicidal compositions according to the present invention are:

aqueous suspension concentrates which comprise from 10 to 70% of one or more compounds of formula (I), from 2 to 10% of surface-active agent, from 0.1 to 5% of thickener and from 15 to 87.9% of water;

wettable powders which comprise from 10 to 90% of one or more compounds of formula (I), from 2 to 10% of surface-active agent and from 8 to 88% of solid diluent or carrier;

water soluble or water dispersible powders which comprise from 10 to 90% of one or more compounds of formula (I), from 2 to 40% of sodium carbonate and from 0 to 88% of solid diluent;

liquid water soluble concentrates which comprise from 5 to 50%, e.g. 10 to 30%, of one or more compounds of formula (I), from 5 to 25% of surface-active agent and from 25 to 90%, e.g. 45 to 85%, of water miscible solvent, e.g. dimethylformamide, or a mixture of water-miscible solvent and water;

liquid emulsifiable suspension concentrates which comprise from 10 to 70% of one or more compounds of formula (I), from 5 to 15% of surface-active agent, from 0.1 to 5% of thickener and from 10 to 84.9% of organic solvent;

granules which comprise from 1 to 90%, e.g. 2 to 10% of one or more compounds of formula (I), from 0.5 to 7%, e.g. 0.5 to 2%, of surface-active agent and from 3 to 98.5%, e.g. 88 to 97.5%, of granular carrier and emulsifiable concentrates which comprise 0.05 to 90%, and preferably from 1 to 60% of one or more compounds of formula (I), from 0.01 to 10%, and preferably from 1 to 10%, of surface-active agent and from 9.99 to 99.94%, and preferably from 39 to 98.99%, of organic solvent.

Herbicidal compositions according to the present invention may also comprise the compounds of formula (I) in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl-)acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-(1,3,5-triazine], 2,4-D [2,4-dichlorophenoxy-acetic acid], dicamba [3,6-dichloro-2-methoxybenzoic acid], difenzoquat [1,2-dimethyl-3,5-diphenyl-pyrazolium salts], flampropmethyl [methyl N-2-(N-benzoyl-3-chloro-4-fluoroanilino)-propionate], fluometuron [N'-3-trifluoro-methylphenyl)-N,N-dimethylurea], isoproturon [N'-(4-isopropylphenyl)-N,N-dimethylurea], insecticides, e.g. synthetic pyrethroids, e.g. permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

According to a further feature of the present invention there is provided an article of manufacture comprising at least one of the 4-benzoylisoxazole derivatives of formula (I) or, as is preferred, a herbicidal composition as hereinbefore described, and preferably a herbicidal concentrate which must be diluted before use, comprising at least one of the 4-benzoylisoxazole derivatives of formula (I) within a container for the aforesaid derivative or derivatives of formula (I), or a said herbicidal composition, and instructions physically associated with the aforesaid container setting out the manner in which the aforesaid derivative or derivatives of formula (I) or herbicidal composition contained therein is to be used to control the growth of weeds. The containers will normally be of the types conventionally used for the storage of chemical substances which are solid at normal ambient temperatures and herbicidal compositions particularly in the form of concentrates, for example cans and drums of metal, which may be internally lacquered, and plastics materials, bottles or glass and plastics materials and, when the contents of the container is a solid, for example granular, herbicidal compositions, boxes, for example of cardboard, plastics materials and metal, or sacks. The containers will normally be of sufficient capacity to contain amounts of the 4-benzoylisoxazole derivative or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.01 kg and 20 kg of active material per hectare in the manner and for the purposes hereinbefore described.

The following Examples illustrate herbicidal compositions according to the present invention:

EXAMPLE C1

A soluble concentrate is formed from:

| | |
|---|---|
| Active ingredient (compound 1) | 20% w/v |
| Potassium hydroxide solution 33% w/v | 10% v/v |
| Tetrahydrofurfuryl alcohol (THFA) | 10% v/v |
| Water | to 100 volumes. | by stirring THFA, active ingredient (compound 1) and 90% volume of water and slowly adding the potassium hydroxide solution until a steady pH 7–8 is obtained then making up to volume with water.

Similar soluble concentrates may be prepared as described above by replacing the isoxazole (compound 1) with other compounds of formula (I).

EXAMPLE C2

A wettable powder is formed from:

| | |
|---|---|
| Active ingredient (compound 1) | 50% w/w |
| Sodium dodecylbenzene sulphonate | 3% w/w |
| Sodium lignosulphate | 5% w/w |
| Sodium formaldehyde alkylnaphthalene sulphonate | 2% w/w |
| Microfine silicon dioxide | 3% w/w and |
| China clay | 37% w/w | by blending the above ingredients together and grinding the mixture in an air jet mill.

Similar wettable powders may be prepared as described above by replacing the isoxazole (compound 1) with other compounds of formula (I).

EXAMPLE C3

A water soluble powder is formed from:

| | |
|---|---|
| Active ingredient (compound 1) | 50% w/w |
| Sodium dodecylbenzenesulphonate | 1% w/w |
| Microfine silicon dioxide | 2% w/w |

| | -continued |
|---|---|
| Sodium bicarbonate | 47% w/w | by mixing the above ingredients and grinding the above mixture in a hammer mill.

Similar water soluble powders may be prepared as described above by replacing the isoxazole (compound 1) with other compounds of formula (I).

The compounds of the invention have been used in herbicidal applications according to the following procedures.

METHOD OF USE OF HERBICIDAL COMPOUNDS a) General

Appropriate quantities of the compounds used to treat the plants were dissolved in acetone to give solutions equivalent to application rates of up to 4000 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| | Approx number of seeds/pot |
|---|---|
| Weed species | |
| 1) Broad-leafed weeds | |
| Abutilon theophrasti | 10 |
| Amaranthus retroflexus | 20 |
| Galium aparine | 10 |
| Ipomoea purpurea | 10 |
| Sinapis arvensis | 15 |
| Xanthium strumarium | 2. |
| 2) Grass weeds | |
| Alopecurus myosuroides | 15 |
| Avena fatua | 10 |
| Echinochloa crus-galli | 15 |
| Setaria viridis | 20. |
| 3) Sedges | |
| Cyperus esculentus | 3. |
| Crop | |
| 1) Broad-leafed | |
| Cotton | 3 |
| Soya | 3. |
| 2) Grass | |
| Maize | 2 |
| Rice | 6 |
| Wheat | 6. |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep, 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

| | Number of plants per pot | Growth stage |
|---|---|---|
| Weed species | | |
| 1) Broad leafed weeds | | |
| Abutilon theophrasti | 3 | 1–2 leaves |
| Amaranthus retroflexus | 4 | 1–2 leaves |
| Galium aparine | 1 | $1^{st}$ whorl |
| Ipomoea purpurea | 3 | 1–2 leaves |
| Sinapis arvensis | 4 | 2 leaves |
| Xanthium strumarium | 1 | 2–3 leaves. |
| 2) Grass weeds | | |
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |
| 3) Sedges | | |
| Cyperus esculentus | 3 | 3 leaves. |
| Crops | | |
| 1) Broad leafed | | |
| Cotton | 2 | 1 leaf |
| Soya | 2 | 2 leaves. |
| 2) Grass | | |
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

The compounds of the invention, used at 4 kg/ha or less, have shown an excellent level of herbicidal activity together with crop tolerance on the weeds used in the foregoing experiments.

When applied pre- or post-emergence at 1000 g/ha, compounds 1 to 90 gave at least 80% reduction in growth of one or more of the weed species.

While the invention has been described in terms of various preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof.

What is claimed is:

1. A compound of the formula:

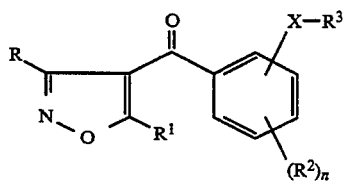

(I)

wherein:
R is hydrogen or —CO$_2$R$^4$;
R$^1$ is:
  straight- or branched-chain alkyl having up to six carbon atoms, optionally substituted by one or more halogen; or
  cycloalkyl having from three to six carbon atoms, optionally substituted by one or more R$^5$ groups or one or more halogen;
R$^2$ is:
  halogen;
  straight- or branched-chain alkyl having up to six carbon atoms, optionally substituted by one or more halogen;
  straight- or branched-chain alkenyl or alkynyl having up to six carbon atoms, optionally substituted by one or more halogen;
  straight- or branched-chain alkyl having up to six carbon atoms which is substituted by one or more —OR$^5$ groups; or
  a member selected from the group consisting of nitro, cyano, —CO$_2$R$^5$, —S(O)$_p$R$^6$, —O(CH$_2$)$_m$OR$^5$, —COR$^5$, —NR$^{61}$R$^{62}$, —N(R$^8$)SO$_2$R$^7$, —OR$^5$, —OSO$_2$R$^7$ and —(CR$^9$R$^{10}$)$_t$—S(O)$_q$R$^7$;
R$^3$ is —S(O)$_q$R$^7$;
X is —(CR$^9$R$^{10}$)$_t$—;
n is zero or an integer from one to four; when n is greater than one, then the R$^2$ groups can be the same or different;
R$^4$ is straight- or branched-chain alkyl having up to 6 carbon atoms, optionally substituted by one or more halogen;
R$^5$ is:
  straight- or branched-chain alkyl having up to 6 carbon atoms, optionally substituted by one or more halogen; or
  straight- or branched-chain alkenyl or alkynyl having from three to six carbon atoms, optionally substituted by one or more halogen;
each of R$^6$, R$^{61}$ and R$^{62}$, which can be the same or different, is:
  straight- or branched-chain alkyl having up to 6 carbon atoms, optionally substituted by one or more halogen;
  phenyl, optionally substituted by from one to five R$^2$ groups, which can be the same or different;
R$^7$ is:
  straight- or branched-chain alkyl having up to 6 carbon atoms, optionally substituted by one or more halogen;
  straight- or branched-chain alkenyl or alkynyl having from three to six carbon atoms, optionally substituted by one or more halogen; or
  —(CR$^{51}$R$^{52}$)$_u$-phenyl, wherein the phenyl portion is optionally substituted by from one to five members, which can be the same or different, selected from the group consisting of halogen; nitro; cyano; straight- or branched-chain alkyl or alkoxy having up to 6 carbon atoms, optionally substituted by one or more halogen; and —S(O)$_p$R$^4$;
R$^8$ is:
  hydrogen; or
  straight- or branched-chain alkyl, alkenyl or alkynyl having up to ten carbon atoms, optionally substituted by one or more halogen;
each of R$^9$ and R$^{10}$, which can be the same or different, is:
  hydrogen;
  straight- or branched-chain alkyl having up to 6 carbon atoms, optionally substituted by one or more halogen; or
  phenyl, optionally substituted by from one to five R$^2$ groups, which can be the same or different;
each of R$^{51}$ and R$^{52}$, which can be the same or different, is:
  hydrogen; or
  straight- or branched-chain alkyl having up to 6 carbon atoms, optionally substituted by one or more halogen;
p is zero, one or two;
q is zero, one or two;
m is 1, 2 or 3;
t is an integer from one to four; when t is greater than one, then the groups —CR$^9$R$^{10}$— can be the same or different; and
u is zero or one;
or an agriculturally acceptable salt thereof.

2. A compound according to claim 1 wherein:
R$^2$ is:
  halogen;
  straight- or branched-chain alkyl having up to six carbon atoms, optionally substituted by one or more halogen;
  straight- or branched-chain alkyl having up to six carbon atoms which is substituted by one or more —OR$^5$ groups; or
a member selected from the group consisting of nitro, cyano, —CO$_2$R$^5$, —S(O)$_p$R$^6$, —O(CH$_2$)$_m$OR$^5$, —COR$^5$, —NR$^{61}$R$^{62}$, —N(R$^8$)SO$_2$R$^7$, —OR$^5$ and —OSO$_2$R$^7$;
R$^5$ is straight- or branched-chain alkyl having up to 6 carbon atoms, optionally substituted by one or more halogen; and
R$^7$ is straight- or branched-chain alkyl having up to 6 carbon atoms, optionally substituted by one or more halogen.

3. A compound according to claim 1 wherein:
R$^1$ is:
  straight- or branched-chain alkyl having up to three carbon atoms; or
  cyclopropyl or 1-methylcyclopropyl;
R$^2$ is:
  halogen;
  straight- or branched-chain alkyl having up to 4 carbon atoms, optionally substituted by one or more halogen;
  straight- or branched-chain alkyl having up to 4 carbon atoms which is substituted by one or more —OR$^5$ groups; or
  a member selected from the group consisting of nitro, cyano, —CO$_2$R$^5$, —S(O)$_p$R$^6$, —O(CH$_2$)$_m$OR$^5$, —NR$^{61}$R$^{62}$, —N(R$^8$)SO$_2$R$^7$, —OR$^5$ and —OSO$_2$R$^7$;

$R^4$ is straight- or branched-chain alkyl having up to 6 carbon atoms, optionally substituted by one or more halogen;

each of $R^5$ and $R^6$, which can be the same or different, is straight- or branched-chain alkyl having up to 4 carbon atoms, optionally substituted by one or more halogen;

each of $R^{61}$ and $R^{62}$, which can be the same or different, is straight- or branched-chain alkyl having up to 6 carbon atoms;

$R^7$ is straight- or branched-chain alkyl having up to 4 carbon atoms, optionally substituted by one or more halogen;

$R^8$ is straight- or branched-chain alkyl, alkenyl or alkynyl having up to 4 carbon atoms, optionally substituted by one or more halogen;

each of $R^9$ and $R^{10}$, which can be the same or different, is:
hydrogen; or
straight- or branched-chain alkyl having up to 6 carbon atoms, optionally substituted by one or more halogen;

n is zero, one or two; and t is one.

4. A compound according to claim 1 wherein:
$R^2$ is:
halogen;
straight- or branched-chain alkyl having up to 4 carbon atoms, optionally substituted by one or more halogen;
straight- or branched-chain alkyl having up to 4 carbon atoms which is substituted by one or more $-OR^5$ groups; or
a member selected from the group consisting of nitro, $-CO_2R^5$, $-S(O)_pR^6$, $-O(CH_2)_mOR^5$, $-NR^{61}R^{62}$, $-N(R^8)SO_2R^7$ and $-OR^5$;

$R^4$ is straight- or branched-chain alkyl having up to 4 carbon atoms;

each of $R^6$, $R^{61}$ and $R^{62}$, which can be the same or different, is straight- or branched-chain alkyl having up to 4 carbon atoms;

$R^7$ is straight- or branched-chain alkyl having up to 4 carbon atoms;

$R^8$ is straight- or branched-chain alkyl having up to 4 carbon atoms, optionally substituted by one or more halogen; and each of $R^9$ and $R^{10}$, which can be the same or different, is:
hydrogen; or
straight- or branched-chain alkyl having up to 4 carbon atoms, optionally substituted by one or more halogen.

5. A compound according to claim 1 wherein:
$R^1$ is methyl, isopropyl or cyclopropyl;
$R^2$ is:
halogen;
straight- or branched-chain alkyl having up to 4 carbon atoms, optionally substituted by one or more halogen;
straight- or branched-chain alkyl having up to 4 carbon atoms which is substituted by one or more $-OR^5$ groups; or
a member selected from the group consisting of $-CO_2R^5$, $-S(O)_pR^6$, $-NR^{61}R^{62}$ and $-OR^5$;

$R^4$ is straight- or branched-chain alkyl having up to 4 carbon atoms;

each of $R^5$, $R^6$, $R^{61}$ and $R^{62}$ which can be the same or different, is straight- or branched-chain alkyl having up to 4 carbon atoms, optionally substituted by one or more halogen;

$R^7$ is straight- or branched-chain alkyl having up to 4 carbon atoms;

each of $R^9$ and $R^{10}$, which can be the same or different, is:
hydrogen; or
straight- or branched-chain alkyl having up to 4 carbon atoms, optionally substituted by one or more halogen; and t is one.

6. A compound according to claim 1 wherein n is greater than zero and the benzoyl ring of the compound of formula (I) is 2,4-disubstituted or 2,3,4-trisubstituted.

7. A compound according to claim 1 wherein n is greater than zero and the benzoyl ring of the compound of formula (I) is 2,3-disubstituted.

8. A compound according to claim 1 wherein:
R is hydrogen or $-CO_2CH_2CH_3$;
$R^1$ is cyclopropyl;
$R^2$ is halogen, $-CF_3$, $-S(O)_pCH_3$ or $-OCH_3$;
X is $-CHR^9-$;
n is zero, one or two;
$R^3$ is $-S(O)_qR^7$ wherein $R^7$ is straight- or branched-chain alkyl or alkenyl having up to four carbon atoms, optionally substituted by from one to three fluorine atoms, or wherein $R^7$ is phenyl;
$R^9$ is hydrogen or methyl; and
each of p and q, which can be the same or different, is zero, one or two.

9. A compound according to claim 1 wherein $R^1$ is straight- or branched-chain alkyl having up to three carbon atoms, cyclopropyl or 1-methylcyclopropyl.

10. A compound according to claim 9 wherein $R^1$ is methyl, isopropyl or cyclopropyl.

11. A compound according to claim 10 wherein $R^1$ is cyclopropyl.

12. A compound according to claim 1 wherein $R^2$ is:
halogen;
straight- or branched-chain alkyl having up to six carbon atoms, optionally substituted by one or more halogen;
straight- or branched-chain alkyl having up to six carbon atoms which is substituted by one or more $-OR^5$ groups; or
a member selected from the group consisting of nitro, cyano, $-CO_2R^5$, $-S(O)_pR^6$, $-O(CH_2)_mOR^5$, $-COR^5$, $-NR^{61}R^{62}$, $-N(R^8)SO_2R^7$, $-OR^5$ and $-OSO_2R^7$.

13. A compound according to claim 12 wherein $R^2$ is:
halogen;
straight- or branched-chain alkyl having up to 4 carbon atoms, optionally substituted by one or more halogen;
straight- or branched-chain alkyl having up to 4 carbon atoms which is substituted by one or more $-OR^5$ groups; or
a member selected from the group consisting of $-CO_2R^5$, $-S(O)_pR^6$, $-NR^{61}R^{62}$ and $-OR^5$.

14. A compound according to claim 13 wherein $R^2$ is halogen, $-CF_3$, $-S(O)_pCH_3$ or $-OCH_3$.

15. A compound according to claim 1 wherein n is zero, one or two.

16. A compound according to claim 1 wherein $R^5$ is straight- or branched-chain alkyl having up to 6 carbon atoms, optionally substituted by one or more halogen.

17. A compound according to claim 16 wherein each of $R^5$ and $R^6$, which can be the same or different, is straight- or branched-chain alkyl having up to 4 carbon atoms, optionally substituted by one or more halogen.

18. A compound according to claim 1 wherein each of $R^{61}$ and $R^{62}$, which can be the same or different, is straight- or branched-chain alkyl having up to 6 carbon atoms.

19. A compound according to claim 1 wherein each of $R^5$, $R^6$, $R^{61}$ and $R^{62}$, which can be the same or different, is straight- or branched-chain alkyl having up to 4 carbon atoms, optionally substituted by one or more halogen.

20. A compound according to claim 1 wherein $R^7$ is straight- or branched-chain alkyl having up to 6 carbon atoms, optionally substituted by one or more halogen.

21. A compound according to claim 20 wherein $R^7$ is straight- or branched-chain alkyl having up to 4 carbon atoms.

22. A compound according to claim 1 wherein $R^7$ is straight- or branched-chain alkyl or alkenyl having up to 4 carbon atoms, optionally substituted by from one to three fluorine atoms, or wherein $R^7$ is phenyl.

23. A compound according to claim 1 wherein $R^8$ is straight- or branched-chain alkyl, alkenyl or alkynyl having up to 4 carbon atoms, optionally substituted by one or more halogen.

24. A compound according to claim 1 wherein each of $R^9$ and $R^{10}$, which can be the same or different, is hydrogen or straight- or branched-chain alkyl having up to 6 carbon atoms, optionally substituted by one or more halogen.

25. A compound according to claim 24 wherein each of $R^9$ and $R^{10}$, which can be the same or different, is hydrogen or straight- or branched-chain alkyl having up to 4 carbon atoms, optionally substituted by one or more halogen.

26. A compound according to claim 1 wherein X is —$CHR^9$—.

27. A compound according to claim 26 wherein $R^9$ is hydrogen or methyl.

28. A compound according to claim 1 wherein each of p and q, which can be the same or different, is zero, one or two.

29. The compound according to claim 1 which is:

4-[4-bromo-2-(methylsulphenylmethyl)benzoyl]-5-cyclopropylisoxazole;
4-[4-bromo-2-(methylsulphonylmethyl)benzoyl]-5-cyclopropylisoxazole;
4-[4-chloro-2-methylsulphenyl-3-(methylsulphenylmethyl)benzoyl]-5-cyclopropylisoxazole;
4-[4-chloro-3-(methylsulphenylmethyl)benzoyl]-5-cyclopropylisoxazole;
4-[4-chloro-2-(methylsulphenylmethyl)benzoyl]-5-cyclopropylisoxazole;
4-[4-bromo-2-(ethylsulphenylmethyl)benzoyl]-5-cyclopropylisoxazole;
5-cyclopropyl-4-[2-methylsulphenylmethyl-4-(trifluoromethyl)benzoyl]isoxazole;
5-cyclopropyl-4-[2-(methylsulphenylmethyl)benzoyl]isoxazole;
5-cyclopropyl-4-[4-methylsulphenyl-2-(methylsulphenylmethyl)benzoyl]isoxazole;
4-[4-bromo-2-(n-propylsulphenylmethyl)benzoyl]-5-cyclopropylisoxazole;
4-[4-bromo-2-(isopropylsulphenylmethyl)benzoyl]-5-cyclopropylisoxazole;
4-[2-(ethylsulphenylmethyl)benzoyl]-5-cyclopropylisoxazole;
5-cyclopropyl-4-[4-fluoro-2-(methylsulphenylmethyl)benzoyl]isoxazole;
4-{4-bromo-2-[(2-propenyl)sulphenylmethyl]benzoyl}-5-cyclopropylisoxazole;
5-cyclopropyl-4-[3-fluoro-4-methoxy-2-(methylsulphenylmethyl)benzoyl]isoxazole;
4-{4-bromo-2-[(2,2,2-trifluoroethyl)sulphenylmethyl]benzoyl}-5-cyclopropylisoxazole;
4-[4-bromo-2-(t-butylsulphenylmethyl)benzoyl]-5-cyclopropylisoxazole;
4-[4-bromo-2-(phenylsulphenylmethyl)benzoyl]-5-cyclopropylisoxazole;
4-[2-chloro-4-(methylsulphenylmethyl)benzoyl]-5-cyclopropylisoxazole;
5-cyclopropyl-4-[2-fluoro-4-(methylsulphenylmethyl)benzoyl]isoxazole;
4-[2-bromo-4-(methylsulphenylmethyl)benzoyl]-5-cyclopropylisoxazole;
5-cyclopropyl-4-[2-methoxy-4-(methylsulphenylmethyl)benzoyl]isoxazole;
5-cyclopropyl-4-[2-methylsulphenyl-4-(methylsulphenylmethyl)benzoyl]isoxazole;
5-cyclopropyl-4-[3,4-dichloro-2-(methylsulphenylmethyl)benzoyl]isoxazole;
4-[3-chloro-4-methylsulphenyl-2-(methylsulphenylmethyl)benzoyl]-5-cyclopropylisoxazole;
5-cyclopropyl-4-[3,4-dichloro-2-(1-methylsulphenyl)ethyl]benzoylisoxazole;
5-cyclopropyl-4-[3,4-dichloro-2-(ethylsulphenylmethyl)benzoyl]isoxazole;
4-[3-bromo-2-(methylsulphenylmethyl)benzoyl]-5-cyclopropylisoxazole;
4-[4-chloro-3-fluoro-2-(methylsulphenylmethyl)benzoyl]-5-cyclopropylisoxazole;
4-[3-bromo-4-chloro-2-(methylsulphenylmethyl)benzoyl]-5-cyclopropylisoxazole;
4-[4-chloro-2-methoxy-3-(methylsulphenylmethyl)benzoyl]-5-cyclopropylisoxazole;
5-cyclopropyl-4-[2,4-dichloro-3-(methylsulphenylmethyl)benzoyl]isoxazole;
4-[2-chloro-4-methylsulphenyl-3-(methylsulphenylmethyl)benzoyl]-5-cyclopropylisoxazole;
4-[4-chloro-3-methylsulphenyl-2-(methylsulphenylmethyl)benzoyl]-5-cyclopropylisoxazole;
5-cyclopropyl-4-[3,4-dichloro-2-(methylsulphinylmethyl)benzoyl]isoxazole;
4-[3-chloro-4-methylsulphenyl-2-(methylsulphinylmethyl)benzoyl]-5-cyclopropylisoxazole;
4-[4-bromo-2-(methylsulphinylmethyl)benzoyl]-5-cyclopropylisoxazole;
5-cyclopropyl-4-{3,4-dichloro-2-[1-(methylsulphinyl)ethyl]benzoyl}isoxazole;
4-[4-chloro-2-(methylsulphinylmethyl)benzoyl]-5-cyclopropylisoxazole;
4-[4-chloro-2-(methylsulphonylmethyl)benzoyl]-5-cyclopropylisoxazole;
4-[4-bromo-2-(ethylsulphinylmethyl)benzoyl]-5-cyclopropylisoxazole;
4-[4-bromo-2-(ethylsulphonylmethyl)benzoyl]-5-cyclopropylisoxazole;
5-cyclopropyl-4-[2-methylsulphinylmethyl-4-(trifluoromethyl)benzoyl]isoxazole;
5-cyclopropyl-4-[2-methylsulphonylmethyl-4-(trifluoromethyl)benzoyl]isoxazole;
5-cyclopropyl-4-[4-methylsulphenyl-2-(methylsulphinylmethyl)benzoyl]isoxazole;
5-cyclopropyl-4-[4-methylsulphonyl-2-(methylsulphonylmethyl)benzoyl]isoxazole;

5-cyclopropyl-4-[2-(methylsulphinylmethyl)benzoyl]isoxazole;
5-cyclopropyl-4-[2-(methylsulphonylmethyl)benzoyl]isoxazole;
5-cyclopropyl-4-[3,4-dichloro-2-(ethylsulphonylmethyl)benzoyl]isoxazole;
5-cyclopropyl-4-[3,4-dichloro-2-(ethylsulphinylmethyl)benzoyl]isoxazole;
4-[4-bromo-2-(n-propylsulphinylmethyl)benzoyl]-5-cyclopropylisoxazole;
4-[4-bromo-2-(n-propylsulphonylmethyl)benzoyl]-5-cyclopropylisoxazole;
4-[bromo-2-(isopropylsulphinylmethyl)benzoyl]-5-cyclopropylisoxazole;
4-[4-bromo-2-(isopropylsulphonylmethyl)benzoyl]-5-cyclopropylisoxazole;
ethyl 4-[4-bromo-2-(methylsulphinylmethyl)benzoyl]-5-cyclopropylisoxazole-3-carboxylate;
ethyl 4-[4-bromo-2-(methylsulphonylmethyl)benzoyl]-5-cyclopropylisoxazole-3-carboxylate;
4-[3-bromo-2-(methylsulphinylmethyl)benzoyl]-5-cyclopropylisoxazole;
4-[3-bromo-2-(methylsulphonylmethyl)benzoyl]-5-cyclopropylisoxazole;
ethyl 4-[3-bromo-2-(methylsulphonylmethyl)benzoyl]-5-cyclopropylisoxazole-3-carboxylate;
ethyl 4-[3-bromo-2-(methylsulphinylmethyl)benzoyl]-5-cyclopropylisoxazole-3-carboxylate;
4-[3-bromo-4-chloro-2-(methylsulphinylmethyl)benzoyl]-5-cyclopropylisoxazole;
4-[3-bromo-4-chloro-2-(methylsulphonylmethyl)benzoyl]-5-cyclopropylisoxazole;
4-[4-chloro-3-fluoro-2-(methylsulphinylmethyl)benzoyl]-5-cyclopropylisoxazole;
4-{4-bromo-2-[(2,2,2-trifluoroethyl)sulphonylmethyl]benzoyl}-5-cyclopropylisoxazole;
4-{4-bromo-2-[(2-propenyl)sulphonylmethyl]benzoyl}-5-cyclopropylisoxazole;
4-{4-bromo-2-[(2-propenyl)sulphinylmethyl]benzoyl}-5-cyclopropylisoxazole;
4-{4-bromo-2-[(1-propenyl)sulphinylmethyl]benzoyl}-5-cyclopropylisoxazole;
4-[4-chloro-3-methylsulphenyl-2-(methylsulphinylmethyl)benzoyl]-5-cyclopropylisoxazole;
4-[4-chloro-3-methylsulphonyl-2-(methylsulphonylmethyl)benzoyl]-5-cyclopropylisoxazole;
4-[4-bromo-2-(t-butylsulphonylmethyl)benzoyl]-5-cyclopropylisoxazole;
4-[4-bromo-2-(phenylsulphonylmethyl)benzoyl]-5-cyclopropylisoxazole;
5-cyclopropyl-4-[2-(ethylsulphinylmethyl)benzoyl]isoxazole;
5-cyclopropyl-4-[2-(ethylsulphonylmethyl)benzoyl]isoxazole;
5-cyclopropyl-4-[3-fluoro-4-methoxy-2-(methylsulphonylmethyl)benzoyl]isoxazole;
4-[4-chloro-3-methylsulphinylmethyl-2-(methoxy)benzoyl]-5-cyclopropylisoxazole;
5-cyclopropyl-4-[2,4-dichloro-3-(methylsulphinylmethyl)benzoyl]isoxazole;
4-[2-chloro-4-(methylsulphinylmethyl)benzoyl]-5-cyclopropylisoxazole;
4-[2-chloro-4-(methylsulphonylmethyl)benzoyl]-5-cyclopropylisoxazole;
5-cyclopropyl-4-[2-fluoro-4-(methylsulphonylmethyl)benzoyl]isoxazole;
4-[2-bromo-4-(methylsulphinylmethyl)benzoyl]-5-cyclopropylisoxazole;
4-[2-bromo-4-(methylsulphonylmethyl)benzoyl]-5-cyclopropylisoxazole;
5-cyclopropyl-4-[2-methoxy-4-(methylsulphonylmethyl)benzoyl]isoxazole;
5-cyclopropyl-4-[2-methylsulphenyl-4-(methylsulphinylmethyl)benzoyl]isoxazole;
4-[3-chloro-4-methylsulphonyl-2-(methylsulphonylmethyl)benzoyl]-5-cyclopropylisoxazole;
5-cyclopropyl-4-[3,4-dichloro-2-(methylsulphonylmethyl)benzoyl]isoxazole;
4-[4-chloro-2-methoxy-3-(methylsulphonylmethyl)benzoyl]-5-cyclopropylisoxazole;
5-cyclopropyl-4-[2,4-dichloro-3-(methylsulphonylmethyl)benzoyl]isoxazole;
ethyl 4-[4-bromo-2-(methylsulphenylmethyl)benzoyl]-5-cyclopropylisoxazole-3-carboxylate;
ethyl 4-[3-bromo-2-(methylsulphenylmethyl)benzoyl]-5-cyclopropylisoxazole-3-carboxylate; or
4-[4-chloro-3-ethylsulphenylmethyl-2-(methylsulphenyl)benzoyl]-5-cyclopropylisoxazole.

30. A herbicidal composition which comprises:
(a) a herbicidally effective amount of a compound of formula (I) as defined in claim 1 or an agriculturally acceptable salt thereof; and
(b) at least one member selected from the group consisting of an agriculturally acceptable carrier and an agriculturally acceptable surface active agent.

31. A herbicidal composition according to claim 30 in the form of an aqueous suspension concentrate, a wettable powder, a water soluble or water dispersible powder, a liquid water soluble concentrate, a liquid emulsifiable suspension concentrate, a granule or an emulsifiable concentrate.

32. A method for controlling the growth of weeds at a locus which comprises applying to said locus a herbicidally effective amount of a compound of formula (I) as defined in claim 1 or an agriculturally acceptable salt thereof.

33. A method according to claim 32 wherein the locus is an area used, or to be used, for the growing of crops and the compound is applied at an application rate of from about 0.01 kg to about 4.0 kg per hectare.

* * * * *